(12) United States Patent
Feling et al.

(10) Patent No.: US 7,928,138 B2
(45) Date of Patent: *Apr. 19, 2011

(54) MARINE ACTINOMYCETE TAXON FOR DRUG AND FERMENTATION PRODUCT DISCOVERY

(75) Inventors: Robert H. R. Feling, Eppstein-Bremthal (DE); William Fenical, Del Mar, CA (US); Paul R. Jensen, San Diego, CA (US); Tracy J. Mincer, Falmouth, MA (US)

(73) Assignee: Regents of the University of California, Oakland, CA (US)

( * ) Notice: Subject to any disclaimer, the term of this patent is extended or adjusted under 35 U.S.C. 154(b) by 90 days.

This patent is subject to a terminal disclaimer.

(21) Appl. No.: 11/966,787

(22) Filed: Dec. 28, 2007

(65) Prior Publication Data

US 2009/0069401 A1 Mar. 12, 2009

Related U.S. Application Data

(63) Continuation of application No. 11/841,588, filed on Aug. 20, 2007, which is a continuation of application No. 11/228,416, filed on Sep. 15, 2005, now abandoned, which is a continuation of application No. 09/991,518, filed on Nov. 16, 2001, now Pat. No. 7,144,723.

(60) Provisional application No. 60/249,356, filed on Nov. 16, 2000, now abandoned.

(51) Int. Cl.
*A61K 31/407* (2006.01)

(52) U.S. Cl. ............... 514/421; 514/255.06; 514/254.11

(58) Field of Classification Search ............. 514/255.06, 514/254.11, 421
See application file for complete search history.

(56) References Cited

U.S. PATENT DOCUMENTS

| | | | |
|---|---|---|---|
| 5,445,829 A | 8/1995 | Paradissis et al. | |
| 5,576,012 A | 11/1996 | Bauer et al. | |
| 5,601,845 A | 2/1997 | Buxton et al. | |
| 5,641,515 A | 6/1997 | Ramtoola | |
| 5,653,987 A | 8/1997 | Modi et al. | |
| 5,654,286 A | 8/1997 | Hostetler | |
| 5,667,809 A | 9/1997 | Trevino et al. | |
| 5,683,676 A | 11/1997 | Akehurst et al. | |
| 5,688,529 A | 11/1997 | Lidgate et al. | |
| 5,707,615 A | 1/1998 | Cardin et al. | |
| 5,707,641 A | 1/1998 | Gertner et al. | |
| 5,726,181 A | 3/1998 | Hausheer et al. | |
| 5,733,888 A | 3/1998 | Carver et al. | |
| 5,756,764 A | 5/1998 | Fenteany et al. | 548/541 |
| 5,874,443 A | 2/1999 | Kiely et al. | |
| 5,886,210 A | 3/1999 | Rayle et al. | |
| 5,922,683 A | 7/1999 | Or et al. | |
| 6,133,308 A | 10/2000 | Soucy et al. | 514/423 |
| 6,147,223 A | 11/2000 | Fenteany et al. | 548/453 |
| 6,214,862 B1 | 4/2001 | Fenteany et al. | 514/423 |
| 6,294,560 B1 | 9/2001 | Soucy et al. | 514/376 |
| 6,333,358 B1 | 12/2001 | Nakazato et al. | 514/650 |
| 6,335,358 B1 | 1/2002 | Fenteany et al. | |
| 6,350,759 B1 | 2/2002 | Casara et al. | |
| 6,458,825 B1 | 10/2002 | Fenteany et al. | 514/421 |
| 6,500,825 B2 | 12/2002 | Lan et al. | |
| 6,506,787 B2 | 1/2003 | Fujishita et al. | |
| 6,509,331 B1 | 1/2003 | Audia et al. | |
| 6,566,553 B2 | 5/2003 | Soucy et al. | 564/123 |
| 6,645,999 B1 | 11/2003 | Schreiber et al. | 514/471 |
| 6,794,516 B2 | 9/2004 | Soucy et al. | 548/239 |
| 6,838,477 B2 | 1/2005 | Schreiber et al. | 514/412 |
| 6,849,743 B2 | 2/2005 | Soucy et al. | 548/531 |
| 7,144,723 B2 | 12/2006 | Fenical et al. | |
| 7,176,232 B2 * | 2/2007 | Fenical et al. | 514/421 |
| 7,176,233 B2 | 2/2007 | Fenical et al. | |
| 7,572,606 B1 | 8/2009 | Lam et al. | |
| 2001/0002391 A1 | 5/2001 | Brand et al. | 514/2 |
| 2001/0051654 A1 | 12/2001 | Elliott et al. | 514/450 |
| 2003/0157695 A1 | 8/2003 | Fenical et al. | |
| 2004/0138196 A1 | 7/2004 | Fenical et al. | 514/192 |
| 2006/0008852 A1 | 1/2006 | Fenical et al. | |
| 2009/0197937 A1 | 8/2009 | Fenical et al. | |
| 2010/0144826 A1 | 6/2010 | Fenical et al. | |

FOREIGN PATENT DOCUMENTS

| | | |
|---|---|---|
| CA | 2429163 | 6/2002 |
| WO | WO 96/32105 | 10/1996 |
| WO | WO 99/09006 | 2/1999 |
| WO | WO 99/15183 | 4/1999 |
| WO | WO 00/23614 | 4/2000 |
| WO | WO 02/47610 | 6/2002 |
| WO | WO 2004/071382 | 8/2004 |
| WO | WO 2005/003137 | 1/2005 |

OTHER PUBLICATIONS

Fenical et al. Powerpoint Presentation, Center for Marine Biotechnology and Biomedicine, Jun. 24, 2001.*
Bernan et al., "Marine Microorganisms as a Source of New Natural Products", *Advances in Applied Microbiology*, 43:57-90 (1997).
Blunt et al., "Marine Natural Products", *Nat. Prod. Rep.*, 20:1-48 (2003).
Bull et al., "Search and Discovery Strategies for Biotechnology: The Paradigm Shift", *Microbiology and Molecular Biology Reviews*, 64:573-606 (Sep. 2000).
Cheng et al., "Arenaric Acid, a New Pentacyclic Polyether Produced by a Marine Bacterium (Actinomycetales)", *J. Nat. Prod.*, 62:605-607 (1999).
Cheng et al., "Luisols A and B, New Aromatic Tetraols Produced by an Estuarine Marine Bacterium of the Genus *Streptomyces* (Actinomycetales)" *J Nat. Prod.*, 62:608-610 (1999).
Colquhoun et al., "Novel Rhodococci and Other Mycolate Actinomycetes from the Deep Sea", *Antonie van Leeuwenhoek*, 74:27-40 (1998).

(Continued)

*Primary Examiner* — James D Anderson
(74) *Attorney, Agent, or Firm* — DLA Piper LLP (US)

(57) ABSTRACT

The invention is the discovery of an actinomycete genus, given the name *Salinospora* gen. nov., that displays an obligate requirement of seawater ($Na^+$) for growth and unique 16S rRNA signature nucleotides. The invention is also the use of the genus for the production and discovery of active biomolecules such as pharmaceutical agents, agrichemicals, immunomodifiers, enzymes and enzyme inhibitors.

4 Claims, 2 Drawing Sheets

OTHER PUBLICATIONS

Colquhoun et al., "Taxonomy and Biotransformation Activities of Some Deep-Sea Actinomycetes", *Extremophiles*, 2:269-277 (1998).
Davidson, "New Dimensions in Natural Products Research: Cultured Marine Microorganisms", *Current Opinion in Biotechnology*, 6:284-291 (1995).
Elliott et al., "Proteasome Inhibition: A New Anti-Inflamatory Strategy", *J. Mol. Med.*, 81:235-245 (2003).
Erba et al., "Mode of Action of Thiocoraline, a Natural Marine Compound With Anti-tumour Activity", *British Journal of Cancer*, 88(7):971-980 (1999).
Feling et al., "Salinosporamide A: A Highly Cytotoxic Proteasome Inhibitor from a Noval Microbial Source, a Marine Bacterium of the New Genus *Salinospora*", *Angew. Chem. Int. Ed.*, 42(3):355-357 (2003).
Fenical, "Chemical Studies of Marine Bacteria: Developing a New Resource", *Chem. Rev.*, 93:1673-1683 (1993).
Fenical, "New Pharmaceuticals from Marine Organisms", *Marine Biotechnology*, 15:339-341 (1997).
Fenical et al., "Marine Microorganisms as a Developing Resource for Drug Discovery", *Pharmaceutical News*, 9:489-494 (2002).
Fernandez-Chimeno et al., "A Novel Cytotoxic Macrolide Produced by a Marine Micromonospora", *Journal of Antibiotics*, 53(5):474-478 (2000).
Fusetani (ed.), "Marine Microorganisms and Drug Discovery: Current Status and Future Potential", *Basel, Karger*, pp. 6-29 (2000).
Goldberg et al., "Not Just Research Tools—Proteasome Inhibitors Offer Therapeutic Promise", *Nature Medicine*, 8(4):338-340 (Apr. 2002).
Goodfellow et al., "Actinomycetes in Biotechnology", Okami et al., ed., *Search and Discovery of new Antibiotics*, Academic Press: San Diego, pp. 33-67 (1988).
Goodfellow et al., "Actinomycetes in Marine Sediments", Ortiz-Ortiz et al., ed., *Biological, Biochemical and Biomedical Aspects of Actinomycetes*, Academic Press: Orlando, pp. 453-472 (1984).
Goodfellow et al., "Search and Discovery of Industrially Significant Actinomycetes", *In Microbial Products: New Approaches*, Society for General Microbiology Symposium No. 44 eds Baumberg et al., Cambridge: Cambridge University Press, pp. 343-383 (1989).
Hardt et al., "Neomarinone, and New Cytotoxic Marinone Derivatives, Produced by a Marine Filamentous Bacterium (Actinomycetales)", *Tetrahedron Letters*, 14(13):2073-2076 (Mar. 2000).
He et al., "Lomaiviticins A and B, Potent Antitumor Antibiotics from *Micromonospora lomaivitiensis*", *J. Am. Chem. Soc.*, 123:5362-5363 (2001).
Helmke et al., "*Rhodococcus marinonascens* Sp. Nov., An Actinomycete From the Sea", *Int. J Syst. Bacteriol*, 34:127-138 (1984).
Horan, "Aerobic Actinomycetes: A Continuing Source of Novel Natural Products", In Gullo, (ed.), *The Discovery of Natural Products With Therapeutic Potential*, Boston: Butterworth-Heineman, pp. 1-30 (1994).
Hopwood, "Genetic Manipulation of *Streptomyces* Polyketide Synthase Genes For Novel Secondary Metabolite Production", *FEMS Microbiol. Rev.*, 16:233-234 (1995).
Jenson et al., "Strategies for the Discovery of Secondary Metabolites from Marine Bacteria: Ecological Perspectives", *Annu. Rev. Microbiol.*, 48:559-584 (1994).
Jensen et al., "The Relative Abundance and Seawater Requirements of Gram Positive Bacteria in Near-Shore Tropical Marine Samples", *Microb. Ecol.*, 29(3):249-257 (1995).
Joseph et al., "Laboratory Cultivation of Widespread and Previously Uncultured Soil Bacteria", *Appl. Environ. Microbiol.* 69(12):7210-7215 (2003).
Koch et al., "16S Ribosomal DNA Analysis of the Genera Micromonospora, Actinoplanes," *Int. Journal of Systematic Bacteriology*, 46:765-768 (1996).
Mincer et al., "Widespread and Persistent Populations of a Major New Marine Actinomycete Taxon in Ocean Sediments", *Appl. Eviron. Microbiol.*, 68(10):5005-5011 (2002).

Moran et al., "Evidence for Indigenous *Streptomyces* Populations in a Marine Environment", *Applied and Environmental Microbiology*, 61(10):3695-3700 (1995).
Nesternenko et al., "*Rhodococcus luteus* Nom, Nov. and *Rhodococcus maris* Nom. Nov.", *Int'l. Journal of Systematic Bacteriology*, 32(1):1-14 (1982).
Nicolaus, "Symbiotic Approach to Drug Design", *Decision Making in Drug Research*, pp. 173-186 (1983).
Nolan et al., "Isolation and Screening of Actinomycetes", *Actinomycetes in Biotechnology*, pp. 1-32 (1988).
O'Donnell, "Recognition of Novel Actinomycetes", *Actinomycetes in Biotechnology*, pp. 69-88 (1988).
Okami et al., "Search and Discovery of New Antibiotics", *Actinomycetes in Biotechnology*, pp. 33-67 (1988).
Okami, "The Search for Bioactive Metabolites from Marine Bacteria", *Journal of Marine Biotechnology*, 1993, vol. 1, pp. 59-65.
Otoguro, "An Integrated Method for the Enrichment and Selective Isolation of *Actinokineospora spp*. In Soil and Plant Litter", *J Appl. Microbiol.*, 92:118-130 (2001).
Page, "Treeview: An Application to Display Phylogenetic Trees on Personal Computers", *Computer Applications in the Biosciences*, 12:357-358 (1996).
Reddy et al., "A Simple Sterocontrolled Synthesis of Salinosporamide A", *J. Am. Chem. Soc.*, 126:6230-6231 (2004).
Rivieccio, "Il Fondo Agli Oceani Potenti Antibiotici E Anticancro", *Newton*, 2003, p. 1.
Romero et al., "Thiocoraline, a New Depsipeptide with Antitumor Activity Produced by a Marine Micromonospora", *The Journal of Antibiotics*, 50(9):734-737 (1997).
Stach et al., "Statistical Approaches for Estimating Actinobacterial Diversity in Marine Sediments", *Appl. Environ. Microbiol.*, 69(10):6189-6200 (2003).
Stach et al., "New Primers for the Class Actinobacteria: Application to Marine and Terrestrial Environments", *Environ Microbiol.*, 5(10):828-841 (2003).
Stackebrandt et al., "Proposal for a New Hierarchic Classification System, Actinobacteria Classis Nov.", *International Journal of Systematic Bacteriology*, 47:479-491 (1997).
Tang et al., "Cloning and Heterologous Expression of the Epothilong Gene Cluster", *Science*, 287:640-642 (2000).
Thompson et al., "Clustal W: Improving the Sensitivity of Progressive Multiple Sequence Alignment through Sequence Weighting", *Nucleic Acids Research*, 22:4673-4680 (1994).
Versalovic et al., "Distribution of Repetitive DNA Sequences in Eubacteria and Application to Fingerpointing of Bacterial Genomes", *Nucleic Acids Res.*, 1991, vol. 19, pp. 6823-6831.
Watve et al., "How Many Antibiotics Are Produced by the Genus *Streptomyces?*" *Arch. Microbiol.*, 176:386-390 (2001).
Weyland, "Distribution of Actinomycetes on the Sea Floor", *Actinomycetes, Zbl. Bakt. Suppl.*, 11:185-193 (1981).
Weyland, "Actinomycetes in North Sea and Atlantic Ocean Sediments", *Nature*, 223:858 (1969).
Zheng et al., "Detection of Antitumor and Antimicrobial Activities in Marine Organism Associated Actinomycetes Isolated from the Taiwan Strait, China", *FEMS Microbiology Letters*, 188:87-91 (2000).
Goodfellow et al., "Ecology of Actinomycetes", *Ann. Rev. Microbiol.*, 37:189-216 (1983).
Jensen et al., "Distribution of Actinomycetes in Near-Shore Tropical Marine Sediments", *Appl. Environ. Microbiol.*, 57:1102-1108 (1991).
Jiang et al., "Actinoflavoside, A Novel Flavonoid-Like Glycoside Produced by a Marine Bacterium of the Genus *Streptomyces*", *Tetrahedron Letters*, 38(29):5065-5068 (1997).
"Cell Lines in the In Vitro Screen" (http://dtp.nci.nih.gov/docs/misc/common_files/cell_list.html, accessed Oct. 27, 2009).
Chauhan et al., "A novel orally active proteasome inhibitor induces apoptosis in multiple myeloma cells with mechanisms distinct from Bortezomib", *Cancer Cell*, 8(5):407-419 (2005).
Cusack et al., "NPI-0052 enhances tumoricidal response to conventional cancer therapy in a colon cancer model", *Clin. Cancer Res.*, 12(22):6758-6764 (2006).

Johnson et al., "Relationships between drug activity in NCI preclinical in vitro and in vivo models and early clinical trials", *Br. J. Cancer*, 84(10):1424-1431 (2001).

Sausville & Burger, "Contributions of human tumor xenografts to anticancer drug development", *Cancer Res.*, 66(7):3351-3354 (2006).

Adams, et al., "Proteasome Inhibitors: A Novel Class of Potent and Effective Antitumor Agents", *Cancer Res.*, (1999) 59:2615-22.

Alessandri, et al., "Mobilization of Capillary Endothelium in Vitro Induced by Effectors of Angiogenesis in Vivo", *Cancer Res.*, (1983) 43(4):1790-1797.

Alm, et al., "Effects of Topically Applied PGF2 and its Isopropylester on Normal and Glaucomatous Human Eyes", *Prog. Clin. Biol. Res.*, (1989) 312:447-58.

Beers et al. (Eds.), The Merck Manual of Diagnosis and Therapy, 17th Ed. 1999, The Merck Research Laboratories, Whitehouse Station N.J., pp. 397-398, 948-949, 1916, 1917, 1974, 1975 and 1978-1983.

Beers, et al., "Bacterial Diseases" *The Merck Research Laboratories*, Whitehouse Station N.J. XP002318189, (1999) 157(13): 1157-1158.

Beers, et al., "Parasitic Infections" *The Merck Research Laboratories*, Whitehouse Station N.J. XP002318189. (1999) Chapter 161, pp. 1241-1252.

Bhalla, et al., "High-Dose Mitoxantrone Induces Programmed Cell Death or Apoptosis in Human Myeloid Leukemia Cells", *Blood*, (1993) 82(10):3133-3140.

Bicknell, et al., "Tumour Angiogenesis", *Oxford University Press*, New York (1997) pp. 5 Content.

Blum, et al., "Adriamycin: A New Anticancer Drug with Significant Clinical Activity", *Ann. Intern Med*, (1974) 80:249-59.

Bradley, et al., "Identification of the Cellular Receptor for Anthrax Toxin", *Nature*, (Nov. 8, 2001) 414(6860):225-9.

Carey, Francis, "Organic Chemistry", 2d ed., *McGraw Hill, Inc.*, New York (1992) 328-331.

Colquhoun, et al, "Rapid Characterization of Deep-Sea Actionmycetes for Biotechnology Screening Programmes", *Antonie Van Leeuwenoek*, (2000) 77:359-67.

Corey et al. "The Structural Requirements for Inhibition of Proteasome Function by the Lactacystin-derived beta-lactone and Synthetic Analogs", *Tetrahedron* (1999) 55(11):3305-3316.

Crane, et al., "A Novel Enantioselective Synthetic Route to Omuralide Analogues with the Potential for Species Selectivity in Proteasome Inhibition", *Organic Letters*, (May 3, 2001) 3(9):1395-1397.

Crueger, et al., (Eds.), "*Biotechnology: A Textbook of Industrial Microbiology*", 2nd ed., *Sinauer Associates, Inc.*, Sunderland MA, (1990), Chapter 2: 4-8.

Cusack, et al., "Enhanced Chemosensitivity to CPT-11 with Proteasome Inhibitor PS-341: Implications for Systemic Nuclear Factor-kB Inhibition", *Cancer Res.*, (May 1, 2001) 61(9):3535-40.

Decker, et al., "Inhibition of Caspase-3-mediated Poly (ADP-ribose) Polymerase (PARP) Apoptotic Cleavage by Human PARP Autoantibodies and Effect on Cells Undergoing Apoptosis", *J. Biol. Chem.*, (2000) 275(12):9043-9046.

Delong, et al. "Environmental Diversity of Bacteria and Archaea", *Syst. Biol.*, (Aug. 2001) 50(4):470-478.

Dick, et al., "Mechanistic Studies on the Inactivation of the Proteasome by Lactacystin", *J Biol Chem.*, (1996) 271(13):7273-76.

Duesbery, et al., "Proteolytic Inactivation of MAP-Kinase-Kinase by Anthrax Lethal Factor", *Science*, (1998) 280:734-7.

Elliott, et al., "The Proteasome: A New Target for Novel Drug Therapies", *American Journal of Clinical Pathology*, (Nov. 2001) 116(5):637-646.

Escuyer, et al., "Anthrax Protective Antigen Interacts with a Specific Receptor on the Surface of CHO-K1 Cells", *Infect Immun.*, (1991) 59(10):3381-6.

Faulkner, D.J., "Marine Natural Products", *Nat Prod Rep*, (Feb. 2001) 18(1):1-49.

Fenteany, et al., "Inhibition of Proteasome Activities and Subunit-Specific Amino-Terminal Threonine modification by Lactacystin", *Science*, (1995) 268:726-73.

Fenteany, et al., "Lactacystin, Proteasome Function, and Cell Fate," *J. Biol. Chem.* (1998) 273:8545.

Fingl, et al., "General Principles," *The Pharmaceutical Basis of Therapeutics*, 5th Ed., (Goodman et al., Eds, 1975), MacMillan Publishing Co. Inc., New York, Chapter 1:1-46.

Folkman, Judah, "Tumor Angiogenesis", *Adv Cancer Res.*, (1985) 43:175-203.

Folkman, Judah, "Angiogenesis-Dependent Diseases", *Seminars in Oncology*, (Dec. 2001) 28:536-42.

Fukuchi, et al., "Direct Proteasome Inhibition by Clasto-Lactacystin B-Lactone Permits the Detection of Ubiquitinated p21 in ML-1 Cells", *Biochem Biophys Acta*, (1999) 1451:206-210.

Gale, et al., "The Molecular Basis of Antibiotic Action", 2nd ed., *John Wiley and Sons*, London (1981) pp. 1-13 Content.

Gantt, et al., "Proteasome Inhibitors Block Development of Plasmodium SPP", *Antimicrobial Agents and Chemotherapy*, (1998) 42(10):2731-2738.

Geier, et al., "A Giant Protease with Potential to Substitute for Some Functions of the Proteasome", *Science*, (1999) 283:978-81.

Gennaro, A.R. ed., *Remington's Pharmaceutical Sciences*, 17th Ed., *Mack Publishing Co.*, Easton, PA, (1985) pp. 5 Contents.

Gennaro, A.R. ed., *Remington's Pharmaceutical Sciences*, 18th Ed., Mack Publishing Co., Easton, PA (1990) pp. 5 Contents.

Giannangeli, et al., "Effect of modifications of the alkylpiperazine moiety of trazodone on 5HT2A and alpha1 receptor binding affinity", *J Med Chem.*, (1999) 42(3):336-45.

Giovannoni, Stephen, "Oceans of Bacteria", *Nature*, (Jul. 29, 2004) 430:515-516.

Golub, et al., "Molecular Classification of Cancer; Class Discovery and Class Prediction by Gene Expression Monitoring", *Science*, (1999) 286:531-537.

Grant, et al., "Intracellular Mechanisms Involved in Basement Membrane Induced Blood Vessel Differentiation in Vitro", *In Vitro Cell Dev. Biol.*, (1991) 27A:327-336.

Hanna, et al., "On the Role of Macrophages in Anthrax", *Proc Natl Acad Sci USA*, (1993) 90:10198-10201.

Harker, et al., "Multidrug Resistance in Mitoxantrone-Selected HL-60 Leukemia Cells in the Absence of P-Glycoprotein Overexpression", *Cancer Res.*, (1989) 15:4542-4549.

Higuchi, et al., "Pro-Drugs as Novel Delivery Systems", vol. 14, A.C.S. Symposium Series *American Chemical Society*, Atlantic City, NJ., Sep. 10, 1974, (1975) pp. 3 Content.

Joshi, A., "Microparticulates for Ophthalmic Drug Delivery", *J Ocul Pharmacol*, (1994) 10:29-45.

Kerr, et al., "Marine Natural Products as Therapeutic Agents", *Exp. Opinion on Therapeutic Patents*, (1999) 9:1207-1223.

King, et al., "How Proteolysis Drives the Cell Cycle", *Science*, (1996) 274:1652-59.

Kisselev, et al., "Proteasome Inhibitors: From Research Tools to Drug Candidates", *Chem Biol*, (Aug. 2001) 8:739-758.

Kozlowski, et al., "Lactacystin Inhibits Cathepsin A Activity in Melanoma Cell Lines", *Tumour Biol*, (Jul./Aug. 2001) 22(4):211-5.

Lam, et al., "Isolation of a Bromo Analog of Rebeccamycin From *Saccharothrix aerocolonigenes*", *J of Antibiotics*, (Sep. 1991) 44(9):934-939.

Lam, et al., "Production, Isolation and Structure Determination of Novel Fluoroindolocarbazoles from *Saccharothrix aerocolonigenes* ATCC 39243", *J of Antibiotics*, (Jan. 2001) 54:1-9.

Lawley, et al., "Induction of Morphologic Differentiation of Endothelial Cells in Culture", *J Investigative Dermatology*, (Aug. 1989) 93(2 Supplement):59S-61S.

Lightcap, et al., "Proteasome Inhibition Measurements Clinical Application", *Clin Chem*, (2000) 46(5):673-683.

Lin, et al., "Cytotoxic Effects of Anthrax Lethal Toxin on Macrophage-Like Cell Line J774A.1", *Curr Microbiol*, (1996) 33:224-227.

Liu, et al., "Precursor Supply for Polyketide Biosynthesis: The Role of Crotonyl-CoA Reductase", *Metab Eng*, (Jan. 2001) 3:40-48.

Mayer, et al., "Efficacy of a Novel Hydrogel Formulation in Human Volunteers", *Ophthalmologica*, (1996) 210(2)101-103.

Mayer, et al., "Marine Pharmacology in 1999: Antitumor and Cytotoxic Compounds." *Anticancer Res.*, (Jul./Aug. 2001) 21(4A):2489-2500.

McMurry, John, *Organic Chemistry*, 5th ed., Brooks/Cole, Pacific Grove, CA. (2000) 398-408.

Meng, et al., "Eponemycin Exerts its Antitumor Effect Through the Inhibition of Proteasome Function," *Cancer Res.*, (1999) 59(12):2798-2801.

Meng, et al., "Epoxomicin, a Potent and Selective Proteasome Inhibitor, Exhibits in Vivo Anti-Inflammatory Activity", *Proc. Natl. Acad. Sci.*, (Aug. 1999) 96:10403-10408.

Min, et al., "Urokinase Receptor Antagonists Inhibit Angiogenesis and Primary Tumor Growth in Syngeneic Mice", *Cancer Res.*, (May 15, 1996) 56(10):2428-2433.

Moore, B.S., "Biosynthesis of Marine Natural Products: Microorganisms and Macroalgae", *Nat Prod Rep.* (1999) 16(6):653-674.

Mordenti, et al., "Intracular Pharmacokinetics and Safety of a Humanized Monoclonal Antibody in Rabbits after Intravitreal Administration of a Solution or a PLGA Microsphere Formulation", *Toxicol. Sci.*, (1999) 52(1):101-106.

Murray, J. Clifford (Ed.), Angiogenesis Protocols (Methods in Molecular Medicine), *Humana Press*, Totowa, NJ. (2001) Index 4 pages.

NCBI website, sequence for EF105548, http://www.ncbi.nlm.nih.gov/entrez/viewer.fcgi?db=nucleotide&val=118640518, 2 pages, downloaded Feb. 15, 2007, 2 pages.

NCBI website, sequence for AB242910, http://www.ncbi.nlm.nih.gov/entrez/viewer.fcgi?db=nucleotide&val=124300751, 2 pages, downloaded Feb. 15, 2007, 2 pages.

NCBI website, Sequence for EF191171, http://www.ncbi.nlm.nih.gov/entrez/viewer.fcgi?db=nucleotide&val=124014014, 2 Pages, downloaded Feb. 15, 2007, 2 pages.

Nicholson, D.W., "ICE/CED 3-Like Proteases as Therapeutic Targets for the Control of Inappropriate Apoptosis", *Nat Biotechnology*, (1996) 14:297-301.

Nicosia, et al., "Growth of Microvessels in Serum-Free Matrix Culture of Rat Aorta: A Quantitative Assay of Angiogenesis In Vitro," *Laboratory Investigation*, (Jul. 1990) 63(1):115-122.

Oikawa, et al., "Angiogenic Factor of a Rat Mammary Tumor Cell Line (RMT-1) (I). Secretion of Two Distinct Angiogenic Factors into Serum-Free Conditioned Medium by RMT-1 Cells", *Cancer Letters*, (1991) 59:57-66.

Omura, et al., "Lactacystin, A novel Microbial Metabolite, induces Neuritogenesis of Neuroblastoma Cells", *J Antibiotics*, (1991) 44:113-116.

O'Neil, M. "The Merck Index Thirteenth Edition" Merck Research Laboratories, Whitehouse Station, N.J. XP002510887, (2001) pp. THER-5, col. 3-pp. THER-7, col. 2.

Ostrowska, et al., "Lactacystin, A Specific Inhibitor of the Proteasome, Inhibits Human Platelet Lysosomal Cathepsin A-like Enzyme." *Biochem Biophys Res Commun*, (1997) 234:729-732.

Ostrowska, et al., "Separation of Cathepsin A-like enzyme and the proteasome: evidence that lactacystin/ B-Lactone is not a specific inhibitor of the Proteasome", *Int J Biochem Cell Biol*, (2000) 32:747-757.

Pagano, et al., "Role of the Ubiquitin-Proteasome Pathway in Regulating Abundance of the Cyclin-Dependent Kinase Inhibitor p27", *Science*, (1995) 269(5224):682-5.

Painter, Robert B., "Inhibition of DNA Replicon Initiation by 4-Nitroquinoline 1-Oxide, Adriamycin, and Ethyleneimine", *Cancer Res.*, (1978) 38(12):4445-9.

Palayoor, et al., "Constitutive Activation of ikB Kinase and NF-kB in Prostate Cancer Cells is Inhibited by Ibuprofen", *Oncogene*, (1999) 18:7389-7394.

Peckham et al., eds. *The Oxford Textbook of Oncology*, published by Oxford University Press, (1995), vol. 1 447-453.

Plunkett, et al., "Methods in Laboratory Investigation: An In Vivo Quantitative Angiogenesis Model Using Tumor Cells Entrapped in Alginate", *Laboratory Investigation*, (Apr. 1990) 62(4):510-517.

Rappe, et al., "Cultivation of the Ubiquitous SAR11 Marine Bacterioplankton Clade", *Nature*, (Aug. 8, 2002) 418:630-633.

Riva, S., "Biocatalytic Modification of Natural Products", *Curr Opin Chem Biol*, (Apr. 2001) 5:106-11.

Roche, Edward B., ed.,."Bioreversible Carriers in Drug Design: Theory and Application", *Pergamon Press*, Elmsford, NY (1987) 14-21.

Rubanyi, Gabor M., "Angiogenesis in Health and Disease: Basic Mechanisms and Clinical Applications", *Marcel Dekker*, New York, NY (1999) pp. 6 Contents.

Sapi, et al., "Simple And Condensed beta-Lactams . . . ". *Collection of Czechoslovak Chemical Communications* (1999) 64(2):190-202.

Schnaper, et al., "Plasminogen Activators Augment Endothelial Cell Organization In Vitro by Two Distinct Pathways", *J. of Cellular Physiology*, (1995) 165:107-118.

Shadomy, et al., "Chemotherapeutics, Antimycotic and Antirickettsial. In: Antibiotics, Chemotherapeutics, and Antibacterial Agents for Disease Control", *John Wiley and Sons*, New York (1982) Index 3 pages.

Shedden, et al., "Efficacy and Tolerability of Timolol Maleate Ophthalmic Gel-Forming Solution Versus Timolol Ophthalmic Solution in Adults with Open-Angle Glaucoma or Ocular Hypertension: A Six-Month, Double Masked, Multicenter Study", *Clin. Ther.*, (Mar. 2001) 23(3):440-50.

Silverman "The Organic Chemistry of Drug Design and Drug Action", *Academic Press*, (1992) pp. 2 & 19-21.

Stackebrandt, et al., "Taxonomic Note: A Place for DNA-DNA Reassociation and 16S rRNA Sequence Analysis in the Present Species Definition in Bacteriology", *Int J Syst Bacteriol.*, (1994) 44(4):846-849.

Streitwieser et al., "Introduction to Organic Chemistry", 2d ed., *Macmillan Publishing Co. Inc.*, New York, NY (1981) 169-171.

Sunwoo, et al., "Novel Proteasome Inhibitor PS-341 Inhibits Activation of Nuclear Factor-kB, Cell Survival, Tumor Growth, and Angiogenesis in Squamous Cell Carcinoma", *Clin Cancer Res.* (May 2001) 7:1419-28.

Tang, et al., "Proteasome Activity is Required For Anthrax Lethal Toxin to Kill Macrophages", *Infection and Immunity.*, (Jun. 1999) 67(6):3055-3060.

Vitale, et al., "Susceptibility of Mitogen-Activated Protein Kinase Kinase Family Members to Proteolysis by Anthrax Lethal Factor", *Biochem J*, (2000) 352(3):739-45.

Vitale, et al., "Anthrax Lethal Factor Cleaves the N-Terminus of MAPKKS and Induces Tyrosine/Threonine Phosphorylation of MAPKS in Cultured Macrophages", *J Applied Microbiology*, (1999) 87:288.

Ward, Bess B., "How Many Species of Prokaryotes are There?", *PNAS*, (Aug. 6, 2002) 99(16):10234-10236.

Wheelis, et al., "On the Nature of Global Classification", *PNAS*, (Apr. 1992) 89:2930-2934.

Woese, Carl R., "Bacterial Evolution", *Microbiological Rev.*, (Jun. 1987) 51(2):221-271.

Zaks, A., "Industrial Biocatalysis", *Curr. Opin. Chem. Biol.*, (Apr. 2001) 5(2):130-6.

Zhang, et al., "Postischemic (6 Hour) Treatment with Recombinant Human Tissue Plaminogen Activator and Proteasome Inhibitor PS-519 Reduces Infarction in a Rat Model of Embolic Focal Cerebral Ischemia", *Stroke*, (Dec. 1, 2001) 32(12): 2926-2931.

\* cited by examiner

SEQUENCE LISTING

```
<160> NUMBER OF SEQ ID NOS: 9

<210> SEQ ID NO 1
<211> LENGTH: 20
<212> TYPE: DNA
<213> ORGANISM: Artificial sequence
<220> FEATURE:
<223> OTHER INFORMATION: Amplification primer

<400> SEQUENCE: 1
agagtttgat cctggctcag                                              20
```

<210> SEQ ID NO 2
<211> LENGTH: 22
<212> TYPE: DNA
<213> ORGANISM: Artificial sequence
<220> FEATURE:
<223> OTHER INFORMATION: Amplification primer

<400> SEQUENCE: 2

```
tacggctacc ttgttacgac tt                                              22
```

<210> SEQ ID NO 3
<211> LENGTH: 1479
<212> TYPE: DNA
<213> ORGANISM: Salinospora sp.
<220> FEATURE:
<221> NAME/KEY: misc_feature
<223> OTHER INFORMATION: CNH643 16S ribosomal RNA gene, partial sequence

<400> SEQUENCE: 3

```
agagtttgat cctggctcag gacgaacgct ggcggcgtgc ttaacacatg caagtcgagc     60
ggaaaggccc ttcggggtac tcgagcggcg aacgggtgag taacacgtga gtaacctgcc    120
ccaggctttg ggataacccc gggaaaccgg ggctaatacc ggatatgacc atctgtcgca    180
tggtgggtgg tggaaagatt ttttggcttg ggatgggctc gcggcctatc agcttgttgg    240
tggggtgatg gcctaccaag gcggcgacgg gtagccggcc tgagagggcg accgccaca    300
ctgggactga gacacggccc agactcctac gggaggcagc agtggggaat cttgcacaat    360
gggcggaagc ctgatgcagc gacgccgcgt gagggatgac ggccttcggg ttgtaaacct    420
ctttcagcag ggacgaagcg tttgtgacgg tacctgcaga agaagcgccg gccaactacg    480
tgccagcagc cgcggtaaga cgtagggcgc aagcgttgtc cggatttatt gggcgtaaag    540
agctcgtagg cggcttgtcg cgtcgactgt gaaaacccgt ggctcaactg cgggcttgca    600
gtcgatacgg gcaggctaga gttcggtagg ggagactgga attcctggtg tagcggtgaa    660
atgcgcagat atcaggagga acaccggtgg cgaaggcggg tctctgggcc gatactgacg    720
ctgaggagcg aaagcgtggg gagcaacag gattagatac cctggtagtc cacgctgtaa    780
acgttgggcg ctaggtgtgg ggggcctctc cggttctctg tgccgcagct aacgcattaa    840
gcgccccgcc tggggagtac ggccgcaagg ctaaaactca aaggaattga cgggggcccg    900
cacaagcggc ggagcatgcg gattaattcg atgcaacgcg aagaacctta cctgggtttg    960
acatcgccgg aaatccttca gagatggggg gtccttcggg gccggtgaca ggtggtgcat   1020
ggctgtcgtc agctcgtgtc gtgagatgtt gggttaagtc cgcaacgag cgcaaccctt   1080
gttcgatgtt gccagcgcgt tatggcgggg actcatcgaa gactgccggg gtcaactcgg   1140
aggaaggtgg ggatgacgtc aagtcatcat gccccttatg tccagggctt cacgcatgct   1200
acaatggccg gtacagtggg ctgcgatacc gtgaggtgga gcgaatccca aaaagccggt   1260
ctcagttcgg atcggggtct gcaactcgac cccgtgaagt cggagtcgct agtaatcgca   1320
gatcagcaac gctgcggtga atacgttccc gggccttgta cacaccgccc gtcacgtcac   1380
gaaagtcggc aacacccgaa gccggtggcc taacccttgt gggggagcc gtcgaaggtg   1440
gggctggcga ttgggacgaa gtcgtaacaa ggtagccgt                           1479
```

<210> SEQ ID NO 4
<211> LENGTH: 1479
<212> TYPE: DNA
<213> ORGANISM: Salinospora sp.
<220> FEATURE:
<221> NAME/KEY: misc_feature
<223> OTHER INFORMATION: CNH646 16S ribosomal RNA gene, partial sequence

```
<400> SEQUENCE: 4
agagtttgat cctggctcag gacgaacgct ggcggcgtgc ttaacacatg caagtcgagc    60
ggaaaggccc ttcggggtac tcgagcggcg aacgggtgag taacacgtga gtaacctgcc   120
ccaggctttg ggataacccc gggaaaccgg ggctaatacc ggatatgacc atctgtcgca   180
tggtgggtgg tggaaagatt ttttggcttg ggatgggctc gcggcctatc agcttgttgg   240
tggggtgatg gcctaccaag gcggcgacgg gtagccggcc tgagagggcg accggccaca   300
ctgggactga gacacggccc agactcctac gggaggcagc agtggggaat cttgcacaat   360
gggcggaagc ctgatgcagc gacgccgcgt gagggatgac ggccttcggg ttgtaaacct   420
cttttcagcag ggacgaagcg tttgtgacgg tacctgcaga agaagcgccg gccaactacg   480
tgccagcagc cgcggtaaga cgtagggcgc aagcgttgtc cggatttatt gggcgtaaag   540
agctcgtagg cggcttgtcg cgtcgactgt gaaaacccgt ggctcaactg cgggcttgca   600
gtcgatacgg gcaggctaga gttcggtagg ggagactgga attcctggtg tagcggtgaa   660
atgcgcagat atcaggagga acaccggtgg cgaaggcggg tctctgggcc gatactgacg   720
ctgaggagcg aaagcgtggg gagcgaacag gattagatac cctggtagtc cacgctgtaa   780
acgttgggcg ctaggtgtgg ggggcctctc cggttctctg tgccgcagct aacgcattaa   840
gcgccccgcc tggggagtac ggccgcaagg ctaaaactca aaggaattga cgggggcccg   900
cacaagcggc ggagcatgcg gattaattcg atgcaacgcg aagaaccttac cctgggtttg   960
acatcgccgg aaatccttca gagatggggg gtccttcggg gccggtgaca ggtggtgcat  1020
ggctgtcgtc agctcgtgtc gtgagatgtt gggttaagtc ccgcaacgag cgcaaccctt  1080
gttcgatgtt gccagcgcgt tatgcgggg actcatcgaa gactgccggg gtcaactcgg  1140
aggaaggtgg ggatgacgtc aagtcatcat gcccccttatg tccagggctt cacgcatgct  1200
acaatggccg gtacagtggg ctgcgatacc gtgaggtgga gcgaatccca aaaagccggt  1260
ctcagttcgg atcggggtct gcaactcgac cccgtgaagt cggagtcgct agtaatcgca  1320
gatcagcaac gctgcggtga atacgttccc gggccttgta cacaccgccc gtcacgtcac  1380
gaaagtcggc aacacccgaa gccggtggcc taacccttgt gggggagcc gtcgaaggtg  1440
gggctggcga ttgggacgaa gtcgtaacaa ggtagccgt                         1479
```

<210> SEQ ID NO 5
<211> LENGTH: 1479
<212> TYPE: DNA
<213> ORGANISM: Salinospora sp.
<220> FEATURE:
<221> NAME/KEY: misc_feature
<223> OTHER INFORMATION: CNH898 16S ribosomal RNA gene, partial sequence

```
<400> SEQUENCE: 5
agagtttgat cctggctcag gacgaacgct ggcggcgtgc ttaacacatg caagtcgagc    60
ggaaaggccc ttcggggtac tcgagcggcg aacgggtgag taacacgtga gtaacctgcc   120
ccaggctttg ggataacccc gggaaaccgg ggctaatacc ggatatgact ggctgccgca   180
tggtggttgg tggaaagatt ttttggcttg ggatgggctc gcggcctatc agcttgttgg   240
tggggtgatg gcctaccaag gcggcgacgg gtagccggcc tgagagggcg accggccaca   300
ctgggactga gacacggccc agactcctac gggaggcagc agtggggaat cttgcacaat   360
gggcggaagc ctgatgcagc gacgccgcgt gagggatgac ggccttcggg ttgtaaacct   420
cttttcagcag ggacgaagcg tttgtgacgg tacctgcaga agaagcgccg gccaactacg   480
tgccagcagc cgcggtaaga cgtagggcgc aagcgttgtc cggatttatt gggcgtaaag   540
```

```
agctcgtagg cggcttgtcg cgtcgactgt gaaaacccgt ggctcaactg cgggcttgca      600
gtcgatacgg gcaggctaga gttcggtagg ggagactgga attcctggtg tagcggtgaa      660
atgcgcagat atcaggagga acaccggtgg cgaaggcggg tctctgggcc gatactgacg      720
ctgaggagcg aaagcgtggg gagcgaacag gattagatac cctggtagtc cacgctgtaa      780
acgttgggcg ctaggtgtgg ggagcctctc cggttctctg tgccgcagct aacgcattaa      840
gcgccccgcc tggggagtac ggccgcaagg ctaaaactca aaggaattga cgggggcccg      900
cacaagcggc ggagcatgcg gattaattcg atgcaacgcg aagaaccttaa cctgggtttg     960 acatcgccgg aaatccttca gagatggggg gtccttcggg gccggtgaca ggtggtgcat     1020
ggctgtcgtc agctcgtgtc gtgagatgtt gggttaagtc ccgcaacgag cgcaacccttt    1080 gttcgatgtt gccagcgcgt tatggcgggg actcatcgaa gactgccggg gtcaactcgg    1140
aggaaggtgg ggatgacgtc aagtcatcat gccccttatg tccagggctt cacgcatgct    1200
acaatgccgg gtacaatggg ctgcgatacc gtgaggtgga gcgaatccca aaaagccggt    1260
ctcagttcgg atcggggtct gcaactcgac cccgtgaagt cggagtcgct agtaatcgca    1320
gatcagcaac gctgcggtga atacgttccc gggccttgta cacaccgccc gtcacgtcac    1380
gaaagtcggc aacacccgaa gccggtggcc taacccttgt gggggagcc gtcgaaggtg     1440 gggctggcga ttgggacgaa gtcgtaacaa ggtagccgt                            1479
```

<210> SEQ ID NO 6
<211> LENGTH: 1480
<212> TYPE: DNA
<213> ORGANISM: Salinospora sp.
<220> FEATURE:
<221> NAME/KEY: misc_feature
<223> OTHER INFORMATION: CNH440 16S ribosomal RNA gene, partial sequence

<400> SEQUENCE: 6

```
agagtttgat cctggctcag gacgaacgct ggcggcgtgc ttaacacatg caagtcgagc       60
ggaaaggccc ttcggggtac tcgagcggcg aacgggtgag taacacgtga gtaacctgcc     120
ccaggctttg ggataacccc gggaaaccgg ggctaatacc ggatatgact ggctgccgca     180
tggtggttgg tggaaagatt ttttggcttg ggatgggctc gcggcctatc agcttgttgg     240
tggggtgatg gcctaccaag gcggcgacgg gtagccggcc tgagagggcg accgccaca     300 ctgggactga gacacggccc agactcctac gggaggcagc agtggggaat cttgcacaat     360
gggcggaagc ctgatgcagc gacgccgcgt gagggatgac ggccttcggg ttgtaaacct     420
ctttcagcag ggacgaagcg tttgtgacgg tacctgcaga agaagcgccg gccaactacg     480
tgccagcagc cgcggtaaga cgtagggcgc aagcgttgtc cggatttatt gggcgtaaag     540
agctcgtagg cggcttgtcg cgtcgactgt gaaaacccgt ggctcaactg cgggcttgca     600
gtcgatacgg gcaggctaga gttcggtagg ggagactgga attcctggtg tagcggtgaa     660
atgcgcagat atcaggagga acaccggtgg cgaaggcggg tctctgggcc gatactgacg     720
ctgaggagcg aaagcgtggg gagcgaacag gattagatac cctggtagtc cacgctgtaa     780
acgttgggcg ctaggtgtgg ggagcctctc cggttctctg tgccgcagct aacgcattaa     840
gcgccccgcc tggggagtac ggccgcaagg ctaaaactca aaggaattga cgggggcccg     900
cacaagcggc ggagcatgcg gattaattcg atgcaacgcg aagaaccttaa cctgggtttg    960 acatcgccgg aaatccttca gagatggggg gtccttcggg gccggtgaca ggtggtgcat    1020
ggctgtcgtc agctcgtgtc gtgagatgtt gggttaagtc ccgcaacgag cgcaacccttt   1080 gttcgatgtt gccagcgcgt tatggcgggg actcatcgaa gactgccggg gtcaactcgg   1140
```

| aggaaggtgg ggatgacgtc aagtcatcat gccccttatg tccagggctt cacgcatgct | 1200 |
| acaatggccg gtacaatggg ctgcgatacc gtgaggtgga gcgaatccca aaaagccggt | 1260 |
| ctcagttcgg atcggggtct gcaactcgac cccgtgaagt cggagtcgct agtaatcgca | 1320 |
| gatcagcaac gctgcggtga atacgttccc gggccttgta cacaccgccc gtcacgtcac | 1380 |
| gaaagtcggc aacacccgaa gccggtggcc taacccttgt gggggagcc gtcgaaggtg | 1440 |
| gggctggcga ttgggacgaa gtcgtaacaa ggtagccgta | 1480 |

<210> SEQ ID NO 7
<211> LENGTH: 1479
<212> TYPE: DNA
<213> ORGANISM: Salinospora sp.
<220> FEATURE:
<221> NAME/KEY: misc_feature
<223> OTHER INFORMATION: CNH536 16S ribosomal RNA gene, partial sequence

<400> SEQUENCE: 7

| agagtttgat cctggctcag gacgaacgct ggcggcgtgc ttaacacatg caagtcgagc | 60 |
| ggaaaggccc ttcggggtac tcgagcggcg aacgggtgag taacacgtga gtaacctgcc | 120 |
| ccaggctttg ggataacccc gggaaaccgg ggctaatacc ggatatgact ggctgccgca | 180 |
| tggtggttgg tggaaagatt ttttggcttg ggatgggctc gcggcctatc agcttgttgg | 240 |
| tggggtgatg gcctaccaag gcggcgacgg gtagccggcc tgagagggcg accgccaca | 300 |
| ctgggactga gacacggccc agactcctac gggaggcagc agtggggaat cttgcacaat | 360 |
| gggcggaagc ctgatgcagc gacgccgcgt gagggatgac ggccttcggg ttgtaaacct | 420 |
| cttttcagcag ggacgaagcg tttgtgacgg tacctgcaga agaagcgccg gccaactacg | 480 |
| tgccagcagc cgcggtaaga cgtagggcgc aagcgttgtc cggatttatt gggcgtaaag | 540 |
| agctcgtagg cggcttgtcg cgtcgactgt gaaaacccgt ggctcaactg cgggcttgca | 600 |
| gtcgatacgg gcaggctaga gttcggtagg ggagactgga attcctggtg tagcggtgaa | 660 |
| atgcgcagat atcaggagga acaccggtgg cgaaggcggg tctctgggcc gatactgacg | 720 |
| ctgaggagcg aaagcgtggg gagcgaacag gattagatac cctggtagtc cacgctgtaa | 780 |
| acgttgggcg ctaggtgtgg ggagcctctc cggttctctg tgccgcagct aacgcattaa | 840 |
| gcgccccgcc tggggagtac ggccgcaagg ctaaaactca aaggaattga cgggggcccg | 900 |
| cacaagcggc ggagcatgcg gattaattcg atgcaacgcg aagaaccta cctgggtttg | 960 |
| acatcgccgg aaatccttca gagatggggg gtccttcggg gccggtgaca ggtggtgcat | 1020 |
| ggctgtcgtc agctcgtgtc gtgagatgtt gggttaagtc ccgcaacgag cgcaacccttt | 1080 |
| gttcgatgtt gccagcgcgt tatggcgggg actcatcgaa gactgccggg gtcaactcgg | 1140 |
| aggaaggtgg ggatgacgtc aagtcatcat gccccttatg tccagggctt cacgcatgct | 1200 |
| acaatggccg gtacaatggg ctgcgatacc gtgaggtgga gcgaatccca aaaagccggt | 1260 |
| ctcagttcgg atcggggtct gcaactcgac cccgtgaagt cggagtcgct agtaatcgca | 1320 |
| gatcagcaac gctgcggtga atacgttccc gggccttgta cacaccgccc gtcacgtcac | 1380 |
| gaaagtcggc aacacccgaa gccggtggcc taacccttgt gggggagcc gtcgaaggtg | 1440 |
| gggctggcga ttgggacgaa gtcgtaacaa ggtagccgt | 1479 |

<210> SEQ ID NO 8
<211> LENGTH: 1479
<212> TYPE: DNA
<213> ORGANISM: Salinospora sp.

```
<220> FEATURE:
<221> NAME/KEY: misc_feature
<223> OTHER INFORMATION: CNH725 16S ribosomal RNA gene, partial sequence

<400> SEQUENCE: 8
agagtttgat cctggctcag dacgaacgct ggcggcgtgc ttaacacatg caagtcgagc      60
ggaaaggccc ttcggggtac tcgagcggcg aacgggtgag taacacgtga gtaacctgcc     120
ccaggctttg ggataacccc gggaaaccgg ggctaatacc ggatatgacc atctgtcgca     180
tggtgggtgg tggaaagatt ttttggcttg ggatgggctc gcggcctatc agcttgttgg     240
tggggtgatg gcctaccaag gcggcgacgg gtagccggcc tgagagggcg accggccaca     300
ctgggactga gacacggccc agactcctac gggaggcagc agtggggaat cttgcacaat     360
gggcggaagc ctgatgcagc gacgccgcgt gagggatgac ggccttcggg ttgtaaacct     420 cttttcagcag ggacgaagcg tttgtgacgg tacctgcaga gaagcgccg gccaactacg      480 tgccagcagc cgcggtaaga cgtagggcgc aagcgttgtc cggatttatt gggcgtaaag     540
agctcgtagg cggcttgtcg cgtcgactgt gaaaacccgt ggctcaactg cgggcttgca     600
gtcgatacgg gcaggctaga gttcggtagg ggagactgga attcctggtg tagcggtgaa     660
atgcgcagat atcaggagga acaccggtgg cgaaggcggg tctctgggcc gatactgacg     720
ctgaggagcg aaagcgtggg gagcgaacag gattagatac cctggtagtc cacgctgtaa     780
acgttgggcg ctaggtgtgg ggggcctctc cggttctctg tgccgcagct aacgcattaa     840
gcgccccgcc tggggagtac ggccgcaagg ctaaaactca aaggaattga cggggcccg      900 cacaagcggc ggagcatgcg gattaattcg atgcaacgcg aagaacctta cctgggtttg     960
acatcgccgg aaatccttca gagatggggg gtccttcggg gccggtgaca ggtggtgcat    1020
ggctgtcgtc agctcgtgtc gtgagatgtt gggttaagtc ccgcaacgag cgcaaccctt    1080
gttcgatgtt gccagcgcgt tatgcgggg actcatcgaa gactgccggg gtcaactcgg    1140
aggaaggtgg ggatgacgtc aagtcatcat gccccttatg tccagggctt cacgcatgct    1200
acaatggccg gtacagtggg ctgcgatacc gtgaggtgga gcgaatccca aaaagccggt    1260
ctcagttcgg atcggggtct gcaactcgac cccgtgaagt cggagtcgct agtaatcgca    1320
gatcagcaac gctgcggtga atacgttccc gggccttgta cacaccgccc gtcacgtcac    1380
gaaagtcggc aacacccgaa gccggtggcc taaccccttgt gggggagcc gtcgaaggtg    1440 gggctggcga ttgggacgaa gtcgtaacaa ggtagccgt                            1479

<210> SEQ ID NO 9
<211> LENGTH: 1479
<212> TYPE: DNA
<213> ORGANISM: Salinospora sp.
<220> FEATURE:
<221> NAME/KEY: misc_feature
<223> OTHER INFORMATION: CNH964 16S ribosomal RNA gene, partial sequence

<400> SEQUENCE: 9
agagtttgat cctggctcag gacgaacgct ggcggcgtgc ttaacacatg caagtcgagc      60
ggaaaggccc ttcggggtac tcgagcggcg aacgggtgag taacacgtga gtaacctgcc     120
ccaggctttg ggataacccc gggaaaccgg ggctaatacc ggatatgacc atctgtcgca     180
tggtgggtgg tggaaagatt ttttggcttg ggatgggctc gcggcctatc agcttgttgg     240
tggggtgatg gcctaccaag gcggcgacgg gtagccggcc tgagagggcg accggccaca     300
ctgggactga gacacggccc agactcctac gggaggcagc agtggggaat cttgcacaat     360
gggcggaagc ctgatgcagc gacgccgcgt gagggatgac ggccttcggg ttgtaaacct     420
```

```
ctttcagcag ggacgaagcg tttgtgacgg tacctgcaga agaagcgccg gccaactacg    480
tgccagcagc cgcggtaaga cgtagggcgc aagcgttgtc cggatttatt gggcgtaaag    540
agctcgtagg cggcttgtcg cgtcgactgt gaaaacctgt ggctcaactg cgggcttgca    600
gtcgatacgg gcaggctaga gttcggtagg ggagactgga attcctggtg tagcggtgaa    660
atgcgcagat atcaggagga acaccggtgg cgaaggcggg tctctgggcc gatactgacg    720
ctgaggagcg aaagcgtggg gagcaacag  gattagatac cctggtagtc cacgctgtaa    780
acgttgggcg ctaggtgtgg ggggcctctc cggttctctg tgccgcagct aacgcattaa    840
gcgccccgcc tggggagtac ggccgcaagg ctaaaactca aaggaattga cgggggcccg    900
cacaagcggc ggagcatgcg gattaattcg atgcaacgcg aagaaccttt cctgggtttg    960
acatcgccgg aaatccttca gagatggggg gtccttcggg gccggtgaca ggtggtgcat   1020
ggctgtcgtc agctcgtgtc gtgagatgtt gggttaagtc ccgcaacgag cgcaacccct   1080
gttcgatgtt gccagcgcgt tatggcgggg actcatcgaa gactgccggg gtcaactcgg   1140
aggaaggtgg ggatgacgtc aagtcatcat gccccttatg tccagggctt cacgcatgct   1200
acaatggccg gtacagtggg ctgcgatacc gtgaggtgga gcgaatccca aaaagccggt   1260
ctcagttcgg atcggggtct gcaactcgac cccgtgaagt cggagtcgct agtaatcgca   1320
gatcagcaac gctgcggtga atacgttccc gggccttgta cacaccgccc gtcacgtcac   1380
gaaagtcggc aacacccgaa gccggtggcc taaccttgt ggggggagcc gtcgaaggtg    1440
gggctggcga ttgggacgaa gtcgtaacaa ggtagccgt                          1479
```

MARINE ACTINOMYCETE TAXON FOR DRUG AND FERMENTATION PRODUCT DISCOVERY

CROSS-REFERENCES TO RELATED APPLICATIONS

This application is a continuation application of U.S. application Ser. No. 11/841,588, filed Aug. 20, 2007, now pending, which is a continuation application Ser. No. 11/228,416, filed Sep. 15, 2005, now abandoned, which is a continuation application of U.S. application Ser. No. 09/991,518 filed Nov. 16, 2001, now issued as U.S. Pat. No. 7,144,723, which claims the benefit under 35 USC §119(e) to U.S. Application Ser. No. 60/249,356 filed Nov. 16, 2000, now abandoned. The disclosure of each of the prior applications is considered part of and is incorporated by reference in the disclosure of this application.

FIELD OF THE INVENTION

The invention relates to the discovery of a novel taxon of marine bacteria of the order Actinomycetales and the use of this taxon for the discovery and production of proteins, secondary metabolites and biomolecules for use as pharmaceutical compositions, agrichemicals, immunomodifiers, enzymes and enzyme inhibitors.

BACKGROUND OF THE INVENTION

Microorganisms belonging to the class Actinobacteria, commonly called actinomycetes, reside taxonomically within the Gram-positive bacteria and are ubiquitous in terrestrial environments. Actinomycetes are a prolific source of diverse biologically active metabolites. They have been a source of a numerous useful products including Pharmaceuticals, agrichemicals, low molecular weight enzyme inhibitors, immunomodifiers, and enzymes for use in a number of industrial applications, from the food industry to paper making. These microorganisms have also been useful in agriculture as a means of pathogen protection and growth enhancement. Although many useful substances have been discovered from soil actinomycetes over the last 60 years, the yield of novel products has drastically decreased as common soil species continually yield previously discovered metabolites. For this reason, there has been a major effort to discover new actinomycete taxa in the hope that these microorganisms will provide a new source of useful products (Bull et al., 2000).

Actinobacteria are one of a number of classes of bacteria. The class Actinobacteria can be further subdivided into six orders, including the Actinomycetales which can be broken down into 10 suborders. Classical methods for determining taxonomic novelty include morphological and physiological criteria such as color, presence or absence of mycelia, hyphal branch characteristics, spore pattern and motility, tolerance of variation in temperature, salinity and pH, and the ability to utilize various substrates. Although these criteria remain an important component of taxonomic analyses, a new and more definitive method to establish strain uniqueness is 16S rDNA sequence analysis, which also provides evolutionary information on the isolate (Stackebrandt, et al., 1997).

Membership of a strain within the class Actinobacteria is indicated by 16S rDNA sequence similarity values above 80%, as determined by comparison of almost complete 16S rDNA sequences with the most deeply branching members of the class, and the presence of signature nucleotides (Stackebrandt, 1997). Signature nucleotides specific for a taxonomic group are chosen for their presence in more than 95% of the members of that group. 16S signature nucleotide sequences can be used on various taxonomic levels, from defining an order of bacteria to the subdivision of families into genera. This method provides a powerful mathematical model of bacterial evolution and an objective, rather than subjective, set of rules by which bacteria may be assigned a taxonomic status within the classification system.

Despite the fact that the oceans cover 70% of the earth's surface, all known actinomycete genera discovered to date have been land dwellers. In fact, only one marine actinomycete species has been described (Helmke and Weyland, 1984) and it belongs to a well-known terrestrial genus. Although actinomycetes have been cultured from marine sediments, it is widely believed that marine isolates are derived from dormant terrestrial spores that were washed into the sea (Goodfellow and Haynes, 1984). The "wash-in" theory was postulated because the marine isolates did not require seawater for growth, were closely related to terrestrial species, and tended to decrease in number with increasing distance from land (Goodfellow and Williams, 1983). Because many terrestrial actinomycetes can tolerate high salinity and pressure, and because of their distribution and physiology, it was concluded that most actinomycetes have been washed into the sea and collect in sediments where they can survive for long periods of time as spores (Goodfellow and Haynes, 1984). These types of studies have led to the general belief that marine actinomycetes are not significantly different from those on land and therefore of little utility as a source of novel industrial products.

SUMMARY OF THE INVENTION

The invention is the discovery, isolation and characterization of the first major obligate marine actinomycete taxon for which the name *Salinospora* gen. nov. is proposed. Members of this genus are readily recognized by a series of characteristic features including:
  1. Obligate requirement of sodium (seawater) for growth.
  2. Presence of at least 4 of the 5 16S rRNA signature nucleotides (Table 3) and close phylogenetic relatedness to the *Salinospora* clade using 16S rRNA treeing methods.
  3. Morphological characteristics typically including:
     a.) colony color ranging from orange to brown,
     b.) no or scant aerial mycelia,
     c.) diffusable melanin-like pigments and spores that blacken the colony surface,
     d.) hyphae that are finely branched and non-fragmenting with spores produced singly or in clusters.
  4. Comparison with a deposit of a type strain CNH646 at the ATCC (American Type Culture Collection; 12301 Parklawn Drive; Rockville, Md. 20852) on Sep. 27, 2000 under number ATCC PTA 250 PTA-2501.

The discovery of the *Salinospora* group refutes prior notions about actinomycetes in the marine environment and provides the first unequivocal evidence that major populations of unique, obligate marine actinomycetes occur widely in ocean sediments. Chemical studies of *Salinospora* group members have led to the isolation of novel compounds and an exceptionally high rate of biologically active extracts indicating that these microorganisms have utility for drug discovery and other industrial applications.

The invention is the use of the novel taxon for the discovery and production of proteins, secondary metabolites and other biomolecules for use in pharmaceutical compositions, agrichemicals, immunomodifiers, enzymes and enzyme inhibitors. Active molecules can be purified from the actinomycetes themselves or metabolites may be purified from the growth media. This genus is a rich source of active biomolecules with many demonstrated pharmacological activities (e.g. antifungal, antimicrobial, anti-cancer). Extracts and products can be used in a number of assays well known to those skilled in the art to determine the activity of the various compounds derived from the actinomycetes.

The invention is the use of the genome of the taxon for the production of biomolecules in the context of the endogenous actinomycete strain or in other organisms. Genes may be expressed singly or in clusters under the control of constitutive or inducible promoters. Genes from the invention may be expressed in heterologous hosts as recombinant or over producing strains. Other portions of the genome, such as transcriptional regulatory elements, can also be used in heterologous contexts for the control of transcription. The genome may be either wild-type or mutant. Mutations may be spontaneous or created in a random or site directed manner by methods well known to those skilled in the art.

The invention is the use of the taxon for the production of gene products from heterologous organisms. Genes may be inserted either singly or in clusters into the actinomycete strains of the invention for expression of proteins, secondary metabolties or other biomolecules. Compounds may be isolated from the actinomycetes or the growth media.

The invention is the use of the taxon for pathogen and pest protection, insecticides, herbicides, microbiocides, growth promotion in agriculture and aquaculture applications. Actinomycetes of the instant invention can compete with harmful micro-organisms in the environment of the plants providing a non-toxic means of protecting plants.

BRIEF DESCRIPTION OF THE DRAWINGS

The present invention will be better understood from the following detailed description of an exemplary embodiment of the invention, taken in conjunction with the accompanying drawings in which like reference numerals refer to like parts and in which.

Applicants made the following biological deposit with the American Type Culture Collection (ATCC), 10801 University Blvd., Manassas, Va. 20110-2209 USA, and International Depositary Authority (IDA) under the terms of the Budapest Treaty on the International Recognition of the Deposit of Microorganisms for the Purposes of Patent Procedure:

| | |
|---|---|
| Definition: | *Actinomycete Salinospora*, strain CNH646 |
| ATCC No.: | PTA-2501 |
| Date of Deposit: | Sep. 27, 2000 |
| Definition: | *Actinomycete Salinospora*, strain CNB440 |
| ATCC No.: | BAA-916 |
| Date of Deposit: | Feb. 4, 2004 |
| Definition: | *Actinomycete Salinospora*, strain CNB536 |
| ATCC No.: | PTA-10582 |
| Date of Deposit: | Jan. 14, 2010 |
| Definition: | *Actinomycete Salinospora*, strain CNH898 |
| ATCC No.: | PTA-5275 (original deposit) |
| Date of Deposit: | Jun. 20, 2003 |
| and | |
| Definition: | *Actinomycete Salinospora*, strain CNH898 |
| ATCC No.: | PTA-10583 (second deposit) |
| Date of Deposit: | Jan. 14, 2010 |

DETAILED DESCRIPTION AND PREFERRED EMBODIMENTS

*Salinospora* strains can be consistently isolated from marine sediments and are distinguished by characteristic signature nucleotides, an obligate requirement of seawater (more specifically, $Na^+$) for growth, and morphological characteristics. Isolates belonging to this group were obtained on five separate occasions from tropical to subtropical, near-shore sediments collected from the Atlantic Ocean, the Red Sea and the Sea of Cortez indicating a world-wide distribution. In these studies, a total of 147 independent sediment samples were evaluated and 51 of these yielded a total of 182 *Salinospora* isolates of which seven were subjected to in-depth physiological and phylogenetic evaluation (Table 1). Subsequently, over 1000 strains have been obtained from additional collections.

Natural location of strains. Select, diverse isolates representing over 1000 strains with *Salinospora* morphology were used for in-depth phylogenetic and physiological analyses. Nearly complete 16S rDNA sequences (>95% of the entire gene) were obtained for all strains listed. Note that CNB394 and CNB512 are marine-derived *Micromonospora* isolates and were carried through analyses to illustrate fundamental differences between *Salinospora* and *Micromonospora* genera.

TABLE 1

| Strain | Year and location | Habitat descrip. and depth | Genus |
|---|---|---|---|
| CNH643 | 1999 Bahamas, Sweetings Cay | Coarse sand, 1 m | *Salinospora* |
| CNH646 | 1999 Bahamas, Andros Island | Spur and grove, 10 m | *Salinospora* |
| CNH725 | 2000 Red Sea, Sha'b el utal | Coarse sand, 20 m | *Salinospora* |
| CNH898 | 2000 Bahamas, Little San Salvador | Coarse sand, 30 m | *Salinospora* |
| CNH964 | 2000 Sea of Cortez Caleta Partida | Coarse sand, 30 m | *Salinospora* |

TABLE 1-continued

| Strain | Year and location | Habitat descrip. and depth | Genus |
|---|---|---|---|
| CNB440 | 1989 Bahamas, Chub Cay | Spur and grove, 20 m | *Salinospora* |
| CNB536 | 1989 Bahamas, Acklins Island | Coarse sand and seagrass, 10 m | *Salinospora* |
| CNB394 | 1989 Bahamas, Chub Cay | Coarse sand and seagrass, 1 m | *Micromonospora* |
| CNB512 | 1989 Bahamas, San Salvador Is. | Spur and grove, 30 m | *Micromonospora* |

All of the 182 *Salinospora* strains tested failed to grow on an agar medium when seawater was replaced with deionized water. Seven phylogenetically diverse strains were further characterized and shown to require sodium for growth (Table 2), a physiological characteristic commonly associated with obligate marine bacteria. Sodium requirements have been studied extensively in Gram-negative marine bacteria and are indicative of highly evolved marine adaptations such as a respiration-dependant sodium ion pump and/or a sodium dependent membrane transport mechanism. The requirement of seawater (sodium) for growth is extremely rare in Gram-positive bacteria and has never before been reported for an actinomycete with the exception of *Rhodococcus marinonascens* (Helmke and Weyland, 1984).

Assay for sodium dependent growth. Physiological growth analysis illustrating fundamental growth differences between *Salinospora* (in bold) and marine-derived *Micromonospora* isolates (CNB394, CNB512) are shown in Table 2. Tests were performed on medium M1 which was found to be optimal for the growth and maintenance of *Salinospora* and *Micromonospora* genera. Isolates were screened using a sterile cotton swab to inoculate macerated, vegetative mycelia onto each analytical medium which was then incubated at 25-28° C. for six to eight weeks. Growth was checked periodically using a Leica stereoscope at 10-64× magnification. All strains grew equally well in natural seawater (NSW) or artificial seawater (ASW Na+). No detectable growth was observed for any of the *Salinospora* isolates on M1 prepared with de-ionized water (D1). The two *Micromonospora* isolates, CNB394 and CNB512, grew better on M1D1 water than on the seawater-based medium. Sodium growth requirements were tested on M1 prepared with ASW in which all sodium sources were replaced with equimolar amounts of potassium (M1, ASW K+). The sodium concentration in seawater of salinity 35 (used for M1, NSW medium in this study) is 450 mM. In order to determine the upper limits of sodium chloride tolerance, strains were tested for growth on M1D1 water in which sodium chloride was added to yield final sodium concentrations of 600 and 1000 mM. The *Salinospora* isolates showed no growth at these elevated sodium levels whereas growth was clearly evident for the marine-derived *Micromonospora* CNB394 and CNB512.

TABLE 2

| | Isolates Tested | | | | | | | | |
|---|---|---|---|---|---|---|---|---|---|
| Medium | CNB 394 | CNB 512 | CNB 440 | CNB 536 | CNB 643 | CNH 646 | CNH 721 | CNH 898 | CNH 964 |
| M1, NSW | + | + | ++ | ++ | ++ | ++ | ++ | ++ | ++ |
| M1, DI H$_2$0 | ++ | ++ | − | − | − | − | − | − | − |
| M1 ASW, Na$^+$ | + | + | ++ | ++ | ++ | ++ | ++ | ++ | ++ |
| M1 ASW K$^+$ | + | + | − | − | − | − | − | − | − |
| 600 mM [Na$^+$] | +/− | +/− | − | − | − | − | − | − | − |
| 1000 mM [Na$^+$] | +/− | +/− | − | − | − | − | | − | − |

*Salinospora* isolates are proving to be a remarkable source of biologically active secondary metabolites. Thus far, of the 105 strains examined, 86% yielded culture extracts with significant cancer cell cytotoxicity (IC$_{50}$ values ranging from 0.004-16.4 micrograms/ml against the HCT-116 human colon carcinoma cell line). Significant antifungal and antibiotic activities have also been observed from the extracts of cultures grown under various conditions with 30% yielding MIC values of 19.5 micrograms/ml or less against amphotericin resistant *Candida albicans* and 35% yielding extract minimum inhibitory concentration (MIC) values of 25 micrograms/ml or less against vancomycin resistant *Enterococcus faecium*.

Figure 1:
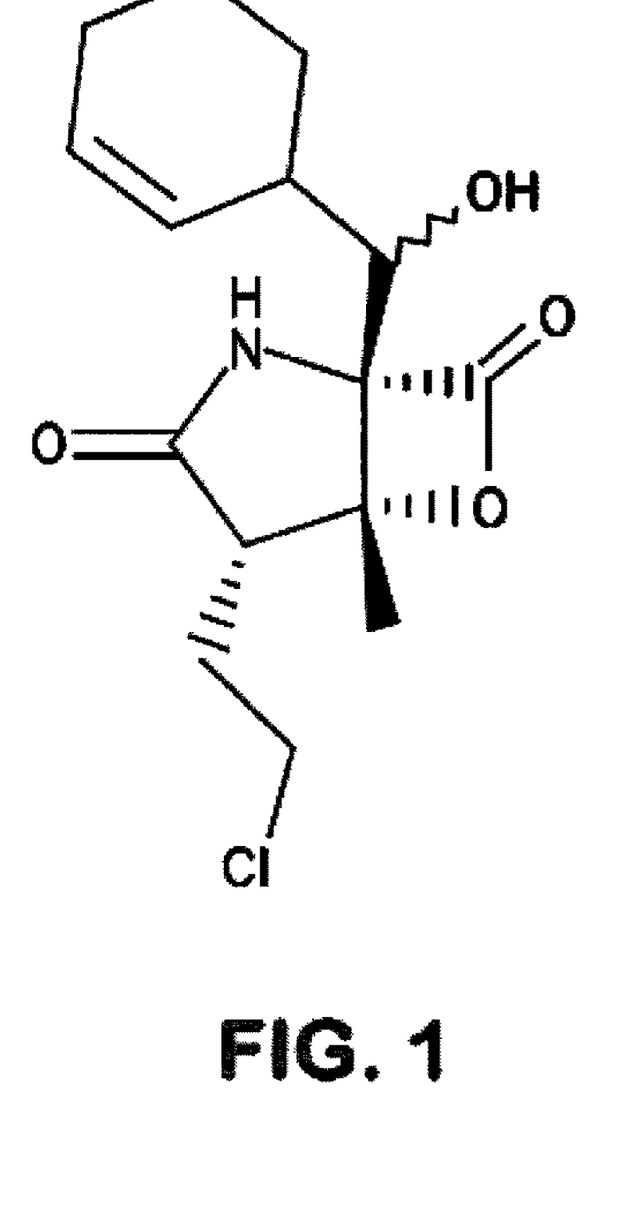
FIG. 1. Structure of salinosporamide A, the first novel, bioactive metabolite obtained from the *Salinospora* group. The isolation of this compound proves that the *Salinospora* group is a resource for unique, biologically active metabolites. The producing strain was cultured in a seawater-based medium and the compound was obtained in pure form following a series of chromatographic steps. The structure of salinosporamide A was elucidated using 1D and 2D nuclear magnetic resonance and high resolution mass spectral data analyses.

Thin layer chromatography and liquid chromatography/mass spectrometric analyses, as well as Repetitive Extragenic Palindrome Polymerase Chain Reaction (REP-PCR), indicate considerable strain to strain chemical and genetic diversity. Bioassay-guided fractionation of one active extract has led to the isolation of a novel series of metabolites that includes a potent cytotoxin (IC$_{50}$=10 ng/ml against the HCT-116 human colon carcinoma cell line) that has been named salinosporamide A (FIG. 1). This molecule is most closely related to clasto-lactacystin beta-lactone (also called omuralide), the intermediary hydrolysis product of lactacystin, an anti-microbial product. Salinosporamide A represents the first natural product to be discovered that possesses a fused beta-lactone gamma-lactam bicyclic ring and is a highly potent anticancer agent.

Figure 2:
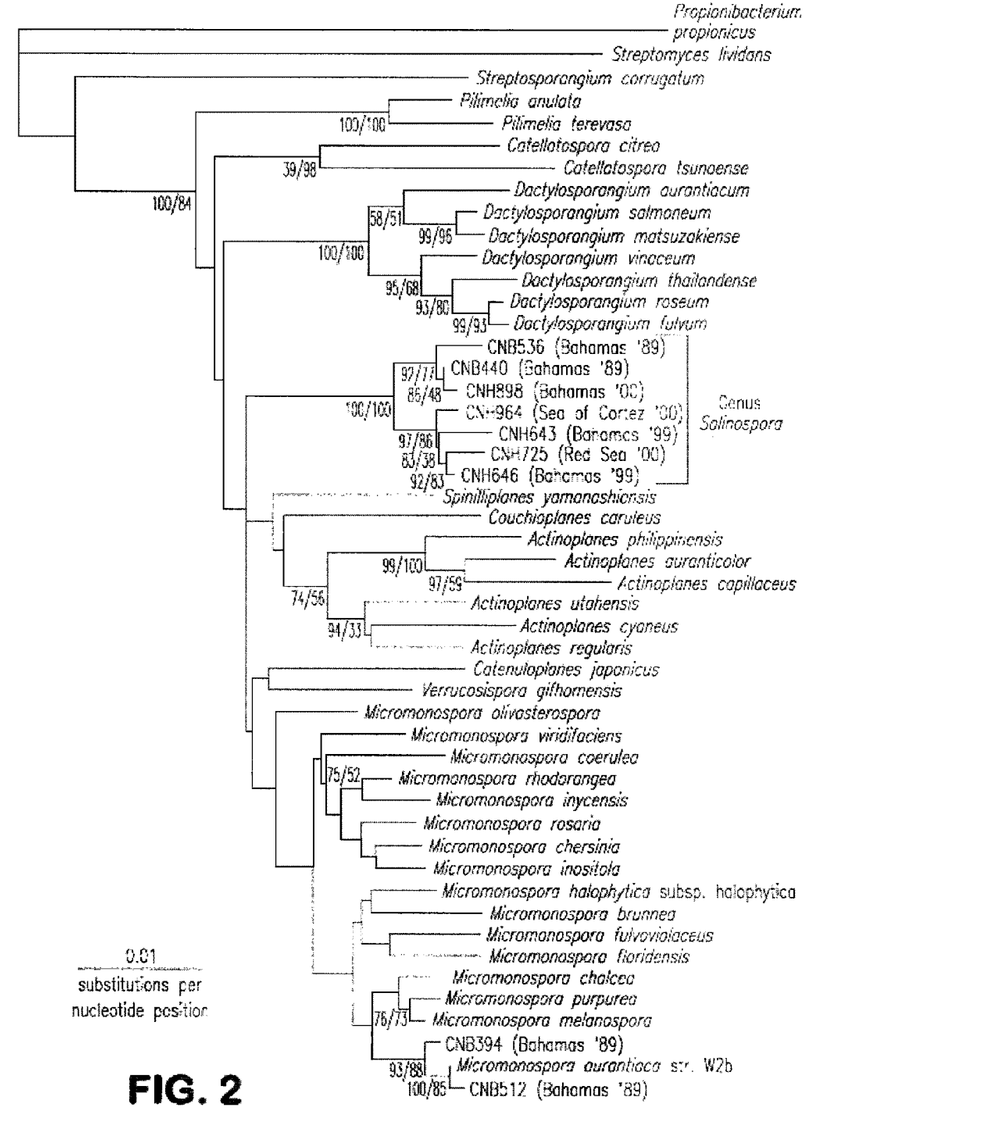
FIG. 2. Phylogenetic dendogram created using the neighbor joining method showing seven diverse members of the *Salinospora* clade along with representatives from all genera officially belonging to the Micromonosporaceae family (Koch, et al; 1996). The distance bar indicates 1 nucleotide substitution per 100 nucleotides. The *Salinospora* clade is shown in the bracket. In parenthesis along side of the *Salinospora* strain designations are the locations and dates of the expeditions from which the isolates were obtained. The *Salinospora* group to date includes 400-500 isolates that showed the characteristic features 1 and 3 (listed in the Background section). These strains are from three expeditions that were grouped first by location and date obtained, then by morphological diversity within each group. From each of these sub-groups, isolates were chosen for almost complete 16S rRNA gene sequencing (greater than 95% of the gene). Phylogenetic programs contained in the Phylip and Clustal W packages were used for analysis and the tree was drawn using Treeview 1.6.1.

The *Salinospora* group was initially recognized after phylogenetic characterization of sediment-derived actinomycetes isolated during an expedition to the Bahamas. Partial 16S rDNA gene sequences from eight morphologically diverse strains indicated the presence of four signature nucleotides between positions 198 to 443 of SEQ ID NOs: 3, 4 and 5, or nucleotide positions 207-468 (based on the *E. coli* 16S rRNA numbering system which is well known to those skilled in the art; see also Table 3 which utilizes the *E. coli* 16S rRNA numbering system to compare the *Salinospora* actinomycetes to those of other Micromonosporaceae genera). These signature nucleotides have subsequently been found in all 45 partially sequenced *Salinospora* strains. Two strains showing the highest phylogenetic diversity (CNH643 and CNH646) were sequenced nearly in their entirety (GenBank accession numbers AY040619 (SEQ ID NO: 3) and AY040620 (SEQ ID NO: 4), respectively) and found to possess one additional signature nucleotide (position 1456) that is also characteristic of this group (Table 3). Phylogenetic analyses of aligned sequences from these strains indicate that they form a distinct and coherent clade within the Micromonosporaceae (FIG. 2). Signature nucleotides unify this clade and a high bootstrap value supports clear separation from the nine currently described genera within the family. SEQ ID NOs: 3 and 4 are identical sequences. SEQ ID NO: 4 is derived from strain CNH646, which was deposited Sep. 27, 2000 (ATCC No. PTA-2501).

16S rRNA signature nucleotides. 16S rRNA signature nucleotides for the genus *Salinospora* and all nine currently accepted genera within the Micromonosporaceae are shown in Table 3. Forty-five diverse *Salinospora* isolates were partially sequenced and confirmed to have all four signature nucleotides at positions 207-468. The signature nucleotide at position 1456 was discovered after subsequent 3' sequencing of the 16S rRNA gene from several (20) *Salinospora* isolates. These are original signatures observed in this study (in addition to those previously published by Koch et al. 1996) that define the coherence of the *Salinospora* clade and separate it from other members of the family. Signature nucleotides were aligned to *E. coli* positions 27-1492 using all existing members of the Micromonosporaceae in the Ribosomal Database Project. Members of the genus *Salinospora* show closest homology to *Micromonospora olivasterospora* (97.1-97.7% similarity), the most deeply rooted member of that genus, with whom they share eight of 12 previously published signature nucleotide positions. Thus *Salinospora* strains are more highly diverged from their closest phylogenetic neighbor than the recently described genus *Verrucosispora giformensis* which shows 98.0% similarity to *Micromonospora olivasterospora* and shares 11 of 12 previously published signature nucleotides.

TABLE 3

| Relative Nucleotide Position of *E. coli* 16S rRNA | All Other Micormonosporaceae Genera | *Salinospora* Isolates | Nucleotide Positions of SEQ ID NOs: 4 and 5 |
|---|---|---|---|
| 207 | (U/C) | A | 198 |
| 366 | (A/G) | C | 351 |
| 467 | (A/G) | U | 442 |
| 468 | A | U | 443 |
| 1456 | A | G | 1423 |

A follow-up study was undertaken in the Bahamas to determine the persistence of the *Salinospora* group. From 20 samples collected from four transects (0-30 m), 355 actinomycetes were observed and over 90% of these displayed characteristic *Salinospora* morphologies suggesting that this group may be the numerically dominant actinomycete in marine sediments. Of those observed, 100 strains were isolated for further study. The average numbers of *Salinospora* colony-forming units (cfu's) ranged from $1.2$-$2.3 \times 10^3$ cfu's/ml sediment. Over 50% of the *Salinospora* isolates appeared on a low nutrient medium (M4) indicating the importance of using appropriate isolation techniques. Thirteen representatives of eight different colony morphotypes were partially sequenced and the most phylogenetically diverse isolate (CNH898) was sequenced nearly in its entirety (GenBank Accession number AY040622) (SEQ ID NO: 5). Strain CNH898 was originally deposited on Jun. 30, 2003 (ATCC No. PTA-5275) and redeposited on Jan. 14, 2010 (ATCC No. PTA-10583).

An examination of 30 actinomycetes with *Salinospora* morphological characteristics that were isolated from the Bahamas in 1989 (Jensen et al, 1991) revealed that all but two of these strains had an obligate requirement of seawater ($Na^+$) for growth. Ten seawater requiring strains representing six different morphotypes were partially sequenced and found to possess the five *Salinospora* signature nucleotides between positions 207-468 (Table 3). The nearly complete 16S rDNA sequence of two of these (CNB440 and CNB536, Gen Bank Accession numbers AY040617 (SEQ ID NO: 6) and AY040618 (SEQ ID NO: 7), respectively) indicates that they are diverse members of the *Salinospora* clade (FIG. 2). Thus, strains belonging to this new taxon have been isolated from near-shore Bahamian sediments on three separate occasions over an 11-year period indicating that they are persistent members of the sediment bacterial community.

The two strains that did not require seawater for growth (CNB394 and CNB512) but had colony morphologies similar to *Salinospora* were found to lack the *Salinospora* signatures in Table 3. Analyses of the almost complete 16S rDNA sequence of these strains showed 99.6-99.9% similarity to *Micromonospora aurantiaca* str. W2b and the presence of all of the signature nucleotides previously published for the genus *Micromonospora* (Koch et al, 1996). The phylogenetic dendogram clearly shows that CNB394 and CNB512 are members of the genus *Micromonospora* (FIG. 2). *Micromonospora* isolates have been reported from marine sediments (Takizawa et al, 1993), including deep-sea samples (Weyland, 1981), however, unlike *Salinospora*, this genus is well known from terrestrial soils and seawater-requiring strains have not been reported.

From extended supra-littoral transects (10 locations, 30 samples) made in the Bahamas (2000 expedition), over 1000 actinomycete colonies were observed including low numbers of Micromonosporaceae (ca. 2%), however none of these required seawater for growth. The inability to recover *Salinospora* strains from supra-littoral samples supports the observation that these bacteria are restricted to the marine environment.

To determine if *Salinospora* members had a broader distribution, sediments were collected from the Red Sea and the Sea of Cortez. From 42 Red Sea sediment samples, 22 isolates with *Salinospora* morphologies and an obligate requirement of seawater for growth were obtained. Six isolates representing 4 major morphotypes were partially sequenced and the almost complete 16S rDNA sequence of one strain (CNH725, GenBank Accession number AY040621) (SEQ ID NO: 8) is represented in FIG. 3. From 36 sediments collected in the Sea of Cortez, 20 seawater-requiring actinomycete strains were isolated and all of these possessed *Salinospora* morphological characteristics. Eight strains representing five different morphotypes were partially sequenced and the phylogenetically diverse isolate CNH964 (GenBank Accession number AY040632 AY040623 (SEQ ID NO: 9)) was sequenced almost in its entirety (FIG. 3). These results clearly indicate that *Salinospora* members are widely distributed in marine sediments.

Phylogenetic analyses and physiological characteristics indicate that the *Salinospora* clade represents a new genus within the family Micromonosporaceae. Although it is unlikely that the diversity within this genus has been revealed in the present study, intra-group 16S rDNA sequence similarity (98.6%) and a robust clade topology indicate that this genus is comprised of multiple species (FIG. 2). Placement of the genus *Salinospora* within the family Micromonosporaceae is supported by the presence of a complete set of family-specific 16S rDNA signature nucleotides (Stackelbrandt, 1997).

Despite evidence that actinomycetes can be recovered from deep-ocean sediments, only one marine species has been described (Helmke and Weyland, 1984) and the inclusion of this group within the autochthonous marine microbiota has not been widely accepted (Bull et al., 2000). Our data provide the first conclusive evidence for the widespread and persistent occurrence in marine sediments of unique populations of obligate marine actinomycetes. Phylogenetic and physiological evidence indicate that these actinomycetes comprise a new taxon and the generic epithet *Salinospora* gen. nov. has been proposed. *Salinospora* strains are a prolific source of biologically active secondary metabolites that are useful for a variety of applications.

Example 1

Sample collection and bacterial isolation. Samples of the top 1 cm of sediment were collected by SCUBA and processed by either stamping, dilution and heat-shock or both methods. Dilution and heat-shock was carried out as follows: 1 ml of wet sediment was added to 4 ml of sterile seawater, heated for six minutes at 55° C., shaken vigorously, and dilutions of $10^{n2}$ to $10^{n4}$ were inoculated onto agar media (M1-M4). For stamping, 10 ml of wet sediment were aseptically placed into a sterile aluminum dish, dried (ca. 24 hours) in a laminar flow hood, ground lightly with a pestle, pressed into a sterile foam plug (14 mm in diameter) and inoculated onto agar media (M1-M4) by stamping 8-9 times in a clockwise fashion giving a serial dilution effect. All isolation media were prepared with 100% filtered natural seawater. Actinomycetes generally appeared after 4-6 weeks of incubation at 25-28° C. and were considered as any colony with a tough leathery texture, dry or folded appearance and branching filaments with or without aerial mycelia. All isolation media had final concentrations of 100 micrograms/ml cycloheximide and 5 micrograms/ml rifampicin added after autoclaving.

Media were prepared by methods well known to those skilled in the art and all contain seawater. Recipes for media are as follows: M1: 10 grams starch, 4 grams yeast extract, 2 grams peptone, 18 grams agar, 1 liter natural seawater; M2: 6 ml glycerol, 1 gram arginine, 1 gram $K_2HPO_4$, 0.5 grams $MgSO_4$ 18 grams agar, 1 liter natural seawater; M3: 6 grams glucose, 2 grams solubilized chitin, 18 grams agar, 1 liter natural seawater; M4: 2 grams solubilized chitin, 18 grams agar, 1 liter natural seawater; M5: 18 grams agar, 1 liter natural seawater.

Example 2

DNA purification, amplification, sequencing and phylogenetic analyses. Genomic DNA was prepared as follows: 10 mg of vegetative mycelia grown on M1 agar for 2-4 weeks at 25-28° C. was macerated and an aqueous cleared lysate, created by standard methods, was precipitated with 0.7 volumes of isopropanol. The resultant DNA pellet was then washed with 70% ethanol and resuspended in 10 mM Tris buffer (pH 8.5) to a final concentration of 100 ng/ml. 16S rDNA sequencing templates were amplified from 10-50 ng of genomic DNA template by the PCR using the primers FC27 (5' AGAGTTTGATCCTGGCTCAG) (SEQ ID NO: 1) and RC1492 (5' TACGGCTACCTTGTTACGACTT) (SEQ ID NO: 2). PCR products were purified with a Qiagen QIAquick PCR clean-up kit using the manufacture's protocols. Partial sequences of morphologically diverse strains were obtained from nucleotides 80-480 (*E. coli* numbering system) using the FC27 primer. Select 16S rDNA amplicons were sequenced almost in their entirety on both top and bottom strands using a total of ten primers. The ten contigs were then assembled yielding gene sequences of 1479 to 1483 unambiguous nucleotides. Hypervariable regions in the 16S rDNA sequences were excluded yielding a total of 1408 aligned nucleotides. 16S rDNA similarity values were calculated by the RDP similarity matrix online analysis and compared to the three nearest neighbors in the RDP database. Sequences were aligned to the secondary structure of members of the Micromonosporaceae in the RDP (Maidak et al, 2001) using the BioEdit software (Hall, 1999). Phylogenetic analyses were performed using the neighbor-joining and parsimony based algorithms in the Clustal W software and PHYLIP software packages, respectively (Thompson et al., 1994; Felsenstein, 1993). The dendogram (FIG. 2) was drawn using Treeview 1.6.1 (Page, 1996).

Example 3

Genetic-analysis by Repetitive Extragenic Palindromic Polymerase Chain Reaction (REP-PCR). The genetic diversity of *Salinospora* strains was analyzed using REP-PCR (Versalovic et al., 1991). This technique, when applied to the *Salinospora* group, involves the use of total genomic DNA as a template and PCR primers specific for repetitive sequences present in the genomes of high G+C content Gram-positive bacteria. The length of the PCR products for any one strain will vary with the position of the repetitive sequences in the genome and result in a population of amplicons of various lengths that when separated on an agarose gel create strain-specific banding patterns. This high throughput method allows for the detection of genetically distinct strains and is more sensitive than 16S rRNA gene analyses as a method to assess genetic diversity. REP-PCR banding patterns are used to sort strains into distinct groups that can produce different gene products. Grouping of strains based on REP-PCR banding patterns correlate well with groups based on the production of secondary metabolites.

Example 4

Production and isolation of useful products. *Salinospora* strains were cultured in multiple sea-water based media including M1 and CKA (starch 5 g, fish hydro-solubles 4 ml, menhaden meal 2 g, kelp powder 2 g, chitosan 2 g, seawater 1 L). An adsorbent resin (XAD-16) was added to the fermentation 24 hours prior to harvest (day 11). The resin was collected by filtration, rinsed with deionized water, and eluted with acetone. Alternatively, cells were collected by filtration, freeze dried and extracted with acetone. The extract was concentrated by rotary evaporation and the residue subjected to C-18 flash chromatography followed by HPLC. The structures of novel fermentation products were resolved using a variety of methods including one- and two-dimensional NMR and mass spectroscopy.

Example 5

Antibacterial assay. Extracts from cultured *Salinospora* strains were tested using standard methods to demonstrate their antibiotic activity against Gram-positive and Gram-negative bacteria. The method used to test against *Staphylococcus aureus* is detailed below. Similar methods are used to test for antimicrobial activity against other organisms. Extracts were compared to known antibiotics and relative activity levels determined. Extracts with potent antibiotic activity were further analyzed for the presence of novel metabolites.

Briefly, cultures of *S. aureus* were grown overnight to stationary phase. The number of bacteria per ml was calculated and a uniform number of bacteria were plated into individual wells containing fresh media. Compounds of interest, including known antibiotic agents (e.g. Oxacillin in DMSO at 0.04 mg/mL), were added to a single row of wells and serially diluted down the plate to determine the concentration required to kill the bacteria. Plates were incubated overnight at 37° C. to allow for cell growth. Samples were read in an automated plate reader at 600 nm and MIC concentrations were determined.

Example 6

Antifungal assay. Extracts from cultured *Salinospora* strains were tested using standard methods to demonstrate antifungal activity against *Candida albicans*. Extracts were compared to known antibiotics and their relative activities determined. Extracts with potent antifungal activity were further analyzed for the presence of novel metabolites.

Briefly, a culture of *C. albicans* was grown overnight to stationary phase. The number of cells per ml was calculated and the suspension was diluted and added to individual wells of 96-well plates. Alamar blue was added to each well as an indicator of viability. Test extracts were added to a single row of wells and serially diluted down the plate to determine the concentration required to kill the fungal cells. Known antifungal agents such as amphotericin were used as a control. Plates were incubated for 12-15 hours at 37° C. Cell concentrations were determined using an automated plate reader at 600 nm and MIC concentrations were determined.

Example 7

Assay for the inhibition of growth of colon carcinoma cells and of ovarian cancer cells in vitro. The cytotoxicity of extracts from cells or culture media were assessed in vitro against the human colon carcinoma cell line HCT116 and the human ovarian carcinoma cell line A2780 by MTS assay. Cells were plated at 4,000 cells per well in 96 well microliter plates and, after 24 hours, the extract (dissolved in DMSO or other appropriate solvent) was added and serially diluted. The cells were incubated with the compound at 37° C. for 72 hours, then the tetrazolium dye MTS was added to a final concentration of 333 µg/ml and the electron coupling agent phenazine methosulfate was added to a final concentration of 25 µM. Once reduced, MTS is converted into a water insoluble blue crystal formazan and that was read at an absorbance at 490 nm with a microplate reader. As dead cells are unable to reduce MTS, the amount of formazan is correlated to the number of viable cells. The $IC_{50}$, the drug concentration required to inhibit proliferation of 50% of the cells, was used as a measure of efficacy.

Example 8

Anti-Herpes Simplex Virus (HSV-1) assay. Antiviral activity can also be determined using an MTS assay. Vero cells were plated into duplicate 96-well plates for infection with virus and cytotoxicity control. One plate of cells was incubated with virus for an hour at 37° C. Both plates were overlaid with a series of concentrations of the extract of interest and plates were incubated for five days. MTS solution was added to the plates and the plates were incubated for three hours as described above. Absorbance at 490 nm was read with a microplate reader and correlated to antiviral activity and cellular toxicity.

Example 9

Chemical mutagenesis of *Salinospora* strains to generate overproducing strains. Chemical mutagenesis of *Salinospora* strains can be performed to generate strains that overproduce a desired product. For example, a strain that produces an antibiotic at a low level is treated with ethylmethylsulfonate (EMS) during the mid-log growth phase. Mutagenized cultures are streaked onto plates to allow for the isolation of individual clones. From the individual clones, cultures are grown and the antibiotic, in a crude or pure form, is isolated. The relative yields of the compounds of interest produced by the mutagenized strains are compared to the original strain to select an overproducing strain.

Example 10

Heterologous gene expression. Actinomycete strains have been useful as hosts for the production of secondary metabolites from other more slowly growing organisms (Tang, et al., 2000). Genes, either singly or in clusters, can be expressed in *Salinospora* strains for the production of proteins or secondary metabolites. Methods for transferring nucleic acids into bacteria are well known by those skilled in the art.

Example 11

Gene cluster isolation and expression. The synthesis of a number of actinmycete antibiotics (e.g. actinorhodin, frenolicin, granaticin, griseusin, octatetracycline, and tetracenomycin) are produced by clustered polyketide synthetase (PKS) genes (Hopwood, 1995). PKS genes are classified into two types of large mutifunctional proteins. In PKS type I genes, the substrate progresses through a number of active sites on a single protein. In PKS type II genes, multiprotein complexes are produced and the substrate progresses from one protein to the next. PKS type II genes have been cloned and expressed in heterologous systems, either in their native groupings or in novel combinations. Combining genes for the synthesis of secondary metabolites from *Salinospora* with genes from other actinomycetes provides a novel method of biologically assisted combinatorial chemistry that can lead to the production of novel small molecules. Also, *Salinospora* biosynthetic genes can be shuffled and expressed in an heterologous host leading to the production of new metabolites. PKS genes are not the only ones that occur in modules. For example, non-ribosomal peptide synthetases are modular as well, and are frequently present in the actinomycetes. Biosynthetic gene clusters from the novel *Salinospora* group can be used as genetic feedstock for the expression of novel molecules in heterologous strains or for the overproduction of native and recombinant gene products.

Example 12

Assay for anti-inflammatory activity. Extracts from *Salinospora* cultures are tested by measuring inhibition of phorbol-induced inflammation (edema) in a mouse ear assays. This is a conventional test which has been accepted as demonstrating a compound's effectiveness in reducing inflammation. The compound is topically applied in acetone to the inside pinnae of the ears of mice in a solution containing an edema-causing irritant, i.e. phorbol 12-myristate 13-acetate (PMA). PMA alone (2 microgram per ear) or in combination with varying amounts of the extract is applied to the left ear (5 mice per treatment group) while an acetone (control) is applied to the right. After a 3-hour and 20-minute incubation at 23° C., the mice are sacrificed, the ears removed, and bores taken and weighed. Edema is measured by subtracting the weight of the right ear (control) from the weight of the left ear

Example 13

Enzyme inhibition assay. Extracts from *Salinospora* strains could be tested for their ability to inhibit enzyme activity. Extracts could be prepared as described above and serial dilutions of the extract added to enzyme-substrate mixtures to determine an $IC_{50}$ for the reaction.

Example 14

Enzyme activity assay. Assays for enzyme activity can be tested by growing *Salinospora* strains in the presence of substrates of interest including, but not limited to chitin, lignin, cellulose, and other recalcitrant biopolymers, etc. Depending on the substrate, assays can be performed to determine the amount of substrate remaining or the amount of product produced.

Example 15

Agriculture/aquaculture protection assay. Assays for the protection of plants from pathogens and general growth enhancement can be performed in a standard greenhouse trial. The strain of interest can be applied to the plant directly or incorporated into the growth media. Plants could be challenged by subjecting them to a pathogen and comparing their growth to control groups treated with a pathogen alone, treated with a *Salinospora* strain alone, or untreated. Rates of growth could be compared to select for strains with the desired activities.

Although an exemplary embodiment of the invention has been described above by way of example only, it will be understood by those skilled in the field that modifications may be made to the disclosed embodiment without departing from the scope of the invention, which is defined by the appended claims.

A Sequence Listing is attached electronically herewith and uploaded via the Electronic Filing System of the United States Patent and Trademark Office. The entire contents of the Sequence Listing are incorporated herein by reference. The file details appear as follows:

(a) "UCSD1630-4SEQLIST.txt"-16 Kilobytes

The Sequence Listing, "UCSD1630-4SEQLIST.txt," was created on Dec. 28, 2007 and was uploaded on Dec. 28, 2007.

REFERENCES

Bull, A. T., A. C. Ward, and M. Goodfellow. 2000. Search and discovery strategies for biotechnology: The paradigm shift. *Microbiology and Molecular Biology Reviews.* 64:573-606.

Felsenstein, J. PHYLIP (Phylogeny Inference Package) version 3.5c. (Distributed by the author. Department of Genetics, University of Washington, Seattle., 1993).

Goodfellow, M., and J. A. Haynes. 1984. Actinomycetes in marine sediments, p. 453-472. In L. Ortiz-Ortiz, L. F. Bojalil, and V. Yakoleff (ed.), Biological, biochemical, and biomedical aspects of actinomycetes. Academic Press, Inc. Orlando.

Goodfellow M. and S. T. Williams. 1983. Ecology of actinomycetes. Ann. Rev. Microbiol. 37:189-216.

Helmke, E. and Weyland, H. 1984. *Rhodococcus marinonascens* sp. nov., an actinomycete from the Sea. Int. J. Syst. Bacteriol. 34:127-38.

Hopwood, D. A. 1995. Genetic manipulation of *Streptomyces* polyketide synthase genes for novel secondary metabolite production. FEMS Microbiol. Rev. 16:233-4.

Jensen, P R., Dwight, R., and Fenical, W. 1991. Distribution of actinomycetes in near-shore tropical marine sediments. Appl. Environ. Microbiol. 57:1102-8.

Koch, C, R. M. Kroppenstedt, F. A. Rainey, and E. Stackebrandt. 1996. 16S ribosomal DNA analysis of the genera *Micromonospora, Actinoplanes, Catellatospora, Catenuloplanes, Couchioplanes, Dactylosporangium*, and *Pilimelia* and emendation of the family Micromonosporaceae. International Journal of Systematic Bacteriology. 46:765-768.

Page, R. D. M. 1996. TREEVIEW: An application to display phylogenetic trees on personal computers. Computer Applications in the Biosciences 12, 357-358.

Stackebrandt, E., F. A. Rainey, and N. L. Ward-Rainey. 1997. Proposal for a new hierarchic classification system, Actinobacteria classis nov. International Journal of Systematic Bacteriology. 47:479-491.

Takizawa, M., Colwell, R. R. & Hill, R. T. 1993. Isolation and diversity of actinomycetes in the Chesapeake Bay. Applied and Environmental Microbiology 59, 997-1002.

Tang, L, Shah, S., Chung, L, Carney, J., Katz, L., Khosla, C, and Julien, B. 2000. Cloning and heterologous expression of the epothilong gene cluster. Science. 287:640-2.

Thompson, J. D., Higgins, D. G. & Gibson, T. J. 1994. CLUSTAL W: Improving the sensitivity of progressive multiple sequence alignment through sequence weighting, position-specific gap penalties and weight matrix choice. Nucleic Acids Research 22:4673-4680.

Versalovic, J., T. Koeuth, and J. R. Lupski. 1991. Distribution of repetitive DNA sequences in eubacteria and application to fingerprinting of bacterial genomes. Nucleic Acids Res. 19:6823-6831.

Weyland, H. 1981. Distribution of actinomycetes on the sea floor. Actinomycetes, Zbl. Bakt. Suppl. 11: 185-193.

The invention claimed is:

1. A purified compound having the structure of formula I:

(I)

2. The compound of claim 1, wherein the compound is isolated from a marine actinomycete of the genus *Salinospora*.

3. The compound of claim 1, wherein the compound is obtained from a marine actinomycete of the genus *Salinospora*.

4. A pharmaceutical composition comprising a pharmaceutically acceptable carrier and a compound having the structure of formula I:

(I)

* * * * *

UNITED STATES PATENT AND TRADEMARK OFFICE
CERTIFICATE OF CORRECTION

PATENT NO. : 7,928,138 B2  
APPLICATION NO. : 11/966787  
DATED : April 19, 2011  
INVENTOR(S) : Feling et al.

Page 1 of 1

It is certified that error appears in the above-identified patent and that said Letters Patent is hereby corrected as shown below:

COLUMN 1, LINE 20

Please insert the following title and paragraph beginning on Line 20 of Column 1 prior to the paragraph entitled "FIELD OF THE INVENTION", specifically:

--GRANT INFORMATION

This invention was made with government support under Grant No. CHE-9807098 awarded by the National Science Foundation. The government has certain rights in the invention.--

Signed and Sealed this  
Twenty-third Day of August, 2011

David J. Kappos  
*Director of the United States Patent and Trademark Office*